(12) United States Patent
Cressman

(10) Patent No.: US 8,979,831 B2
(45) Date of Patent: Mar. 17, 2015

(54) THERMOCHEMICAL ABLATION SYSTEM USING HEAT FROM DELIVERY OF ELECTROPHILES

(75) Inventor: Erik N. K. Cressman, Lake Elmo, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1082 days.

(21) Appl. No.: 13/056,376

(22) PCT Filed: Jul. 29, 2009

(86) PCT No.: PCT/US2009/052033
§ 371 (c)(1),
(2), (4) Date: Feb. 24, 2011

(87) PCT Pub. No.: WO2010/014658
PCT Pub. Date: Feb. 4, 2010

(65) Prior Publication Data
US 2011/0152852 A1    Jun. 23, 2011

Related U.S. Application Data

(60) Provisional application No. 61/085,341, filed on Jul. 31, 2008.

(51) Int. Cl.
*A61B 18/06* (2006.01)
*A61K 9/00* (2006.01)
(Continued)

(52) U.S. Cl.
CPC .............. *A61B 18/06* (2013.01); *A61K 9/0019* (2013.01); *A61B 2018/00577* (2013.01); *A61B 2018/068* (2013.01); *A61B 2018/1425* (2013.01); *A61M 25/003* (2013.01); *A61M 2025/0037* (2013.01)

USPC ................ 606/27; 606/28; 604/82; 604/113; 604/257

(58) Field of Classification Search
CPC ............. A61B 18/06; A61B 2018/068; A61B 2018/00577; A61B 2025/0037
USPC ................ 606/27, 28; 604/82, 113, 257, 506
See application file for complete search history.

(56) References Cited

U.S. PATENT DOCUMENTS 5,045,056 A    9/1991  Behl
5,797,869 A    8/1998  Martin et al.
(Continued)

FOREIGN PATENT DOCUMENTS

JP    2002502278 A    1/2002
JP    2005-506101 A    3/2005
(Continued)

OTHER PUBLICATIONS

Castaneda et al., "Cytotoxicity of millimolar concentrations of ethanol on HepG2 human tumor cell line compared to normal rat hepatocytes in vitro," J. Cancer Res. Clin. Oncol., 126(9):503-510, Sep. 2000.

(Continued)

*Primary Examiner* — Linda Dvorak
*Assistant Examiner* — Jocelyn D Ram
(74) *Attorney, Agent, or Firm* — Fish & Richardson P.C.

(57) ABSTRACT

Thermochemical ablation techniques may provide ablation of bodily tissue using chemical reaction energy. The chemical reaction energy is provided by chemical reactions including a highly reactive electrophilic reagent provided to a target tissue location.

38 Claims, 7 Drawing Sheets

(51) Int. Cl.
*A61B 18/00* (2006.01)
*A61B 18/14* (2006.01)
*A61M 25/00* (2006.01)

(56) References Cited

U.S. PATENT DOCUMENTS

| | | |
|---|---|---|
| 6,165,201 A | 12/2000 | Sawhney |
| 6,626,902 B1 | 9/2003 | Kucharczyk et al. |
| 6,673,093 B1* | 1/2004 | Sawhney ............. 606/214 |
| 6,824,555 B1 | 11/2004 | Towler |
| 6,958,059 B2 | 10/2005 | Zadno-Azizi |
| 8,343,095 B2* | 1/2013 | Cressman ............. 604/82 |
| 8,585,691 B2 | 11/2013 | Cressman |
| 8,734,406 B2* | 5/2014 | Cressman ............. 604/257 |
| 8,814,853 B2* | 8/2014 | Bosel ............. 606/28 |
| 2002/0120238 A1* | 8/2002 | McGuckin et al. ............. 604/187 |
| 2002/0143302 A1* | 10/2002 | Hinchliffe et al. ............. 604/272 |
| 2003/0187411 A1 | 10/2003 | Constantz |
| 2003/0226566 A1 | 12/2003 | Dhuper et al. |
| 2004/0166062 A1 | 8/2004 | Roberts et al. |
| 2005/0187542 A1* | 8/2005 | Auge et al. ............. 606/32 |
| 2006/0079869 A1 | 4/2006 | Bischof et al. |
| 2006/0177923 A1* | 8/2006 | Kane et al. ............. 435/325 |
| 2007/0191781 A1 | 8/2007 | Richards et al. |
| 2008/0171982 A1 | 7/2008 | Mehier |
| 2010/0010473 A1 | 1/2010 | D'Alessio et al. |
| 2012/0046656 A1* | 2/2012 | Brannan ............. 606/28 |
| 2012/0253192 A1 | 10/2012 | Cressman |
| 2013/0131659 A1 | 5/2013 | Cressman |
| 2014/0214017 A1* | 7/2014 | Brannan ............. 606/28 |
| 2014/0221830 A1* | 8/2014 | Cressman ............. 600/431 |
| 2014/0276577 A1* | 9/2014 | Thralls ............. 604/506 |
| 2014/0276716 A1* | 9/2014 | Melsheimer ............. 606/28 |

FOREIGN PATENT DOCUMENTS

| | | |
|---|---|---|
| JP | 2011-527607 A | 11/2011 |
| WO | WO9852480 A1 | 11/1998 |
| WO | WO0009199 A1 | 2/2000 |
| WO | WO02067796 A1 | 9/2002 |
| WO | WO03080151 A2 | 10/2003 |
| WO | WO2008108357 A1 | 8/2008 |
| WO | 2008/016357 | 9/2008 |
| WO | WO2008106357 A1 | 9/2008 |
| WO | WO2010014658 A1 | 2/2010 |

OTHER PUBLICATIONS

Castaneda and Kinne, "Short exposure to millimolar concentrations of ethanol induces apoptotic cell death in multicellular HepG2 spheroids," J. Cancer. Res. Clin. Oncol., 126(6):305-310, Jun. 2000.

Kim et al., "Combined radiofrequency ablation and hot saline injection in rabbit liver," Invest Radiol., 38(11)725-732, Nov. 2003.

International Preliminary Report on Patentability for PCT/US2009/052003, issued Feb. 1, 2011, 10 pages.

Office Action for Japanese App. No. 2011-521264, mailed May 27, 2013, 6 pages.

Office Action for Australian App. No. 2009276661, issued Dec. 6, 2013, 4 pages.

Araki et al., "Hepatocellular carcinoma treated by percutaneous hot saline injection," *Oncology Reports*, 12: 569-571.

Arrivé et al., "Percutaneous Acetic Acid Injection for Hepatocellular Carcinoma: Using CT Fluroscopy to Evaluate Distribution of Acetic Acid Mixed with an Iodinated Contrast Agent," *American Roentgen Ray Society*, AJR:180, Jan. 2003.

Clark et al., "Chemical Ablation of Hepatocellular Carcinoma," *JVIR*, vol. 13, No. 9, Part 2, Sep. 2002, pp. S246-S252.

Cressman, E.N.K., "A New Hydrophobic Gel Phantom Gel for Study of Thermochemical Ablation: Initial Results Using a Weak Acid and Weak Base," Abstract 434, p. S154, *2007 SIR Annual Scientific meeting*, Mar. 1-6, 2007, Seattle, WA.

Finch, et al., "The use of a 'Liquid' Electrode in Hepatic Electrolysis," *Journal of Surgical Research*, 120, 272-277 (2004).

Frank et al., Exothermic Electrophiles for Thermochemical Ablation Assessed in a Gel Phantom,: *SIR 2008 Annual Scientific Meeting*, Abstract No. 278, 1 page.

Glinos, et al., "Cytokinetic and Cytotoxic Effects of Urea on HeLa Cells in Suspension Cultures," *J. Nat'l Cancer Inst.*, 71: 1211-1219, Dec. 1982.

Goldberg et al., " Radio-Frequency Thermal Ablation with NaCl Solution Injection: Effect of Electrical Conductivity on Tissue Heating and Coagulation—Phantom and Porcine Liver Study," *Radiology*, 2001; 219:157-165.

Kurokohchi et al. "Percutaneous ethanol and lipiodol injection therapy for hepatocellular carcinoma," *International Journal of Oncology*, 24: 381-387, 2004.

Liao et al., "Radiofrequency ablation after transarterial embolization as therapy for patients with unresectable hepatocellular carcinoma," *Journal of Cancer Surgery*, EJSO 34 (2008) 61-64.

Lubienski et al. "Radiofrequency Thermal Ablation: Increase in Lesion Diameter with Continuous Acetic Acid Infusion" *Cadiovasc Intervent Radiol* (2005) Sep. 23, 2005, 28:789-794.

Nanz, et al., "Contrast Material—enhanced Visualization of the Ablation Medium for Magnetic Resonance—monitored Ethanol Injection Therapy: Imaging and Safety Aspects," *J. Vascular and Interventional Radiology*, vol. 17(1) Jan. 2006. 95-102.

Parmley, et al., "The Possible Deleterious Effects of the Intramymetrial Injection of Hypertonic Urea," *Obstetrics & Gynecology*, Jun. 16, 1975, 3 pages.

Puls, et al., "Laser-Induced Thermotherapy (LITT) of Liver metastases: MR-Guided Percutaneous Insertion of an MRI-compatible Irrigated Microcatheter System Using a Closed High-Field Unit," *Journal of Magnetic Resonance Imaging*, 17:663-670, (2003).

Weinberg et al., "Combined radiofrequency ablation and doxorubicin-eluting polymer implants for liver cancer treatment," Published online Nov. 21, 2006 in Wiley InterScience (www.intersecience.wiley.com) 9 pages.

Wilson, Elizabeth, "A Renaissance for Hofmeister," *Chemical & Engineering News: Science & Technology*, Nov. 26, 2007, vol. 85, No. 48, pp. 47-49.

Young, et al., "Combined Radiofrequency Ablation and Hot Saline Injection in Rabbit Liver," *Investigative Radiology*, col. 38, No. 11, Nov. 2003, pp. 725-732.

International Search Report & Written Opinion, PCT/US2009/052033, mailed Nov. 30, 2009, 32 pages.

Clark et al.., "Chemical Ablation of Liver Cancer," *Techiques in Vascular and Interventional Radiology*, I vol. 10, No. 1, Oct. 31, 2007, pp. 58-63.

Hiltbrand et al. Anticancer Research, 2004. vol. 24, Issue 5A, pp. 2757-2763.

* cited by examiner

THERMOCHEMICAL ABLATION SYSTEM USING HEAT FROM DELIVERY OF ELECTROPHILES

CROSS-REFERENCE TO RELATED APPLICATIONS

This application is a National Stage application under 35 U.S.C. §371 and claims benefit under 35 U.S.C. §119(a) of International Application No. PCT/US2009/052033 filed on Jul. 29, 2009, which claims the benefit of U.S. Provisional Application 61/085,341, filed Jul. 31, 2008. The disclosure of the prior application is considered part of and is hereby incorporated in its entirety by reference in the disclosure of this application.

TECHNICAL FIELD

This document relates to delivery of one or more chemical agents to targeted bodily tissue, for example, to provide thermochemical ablation therapy.

BACKGROUND

A number of ablation treatments have been used to treat tumors or other tissue in a patient's body. In some cases, ablation therapy may be used to treat tumors that are not responsive to chemotherapy or other techniques. For example, primary liver cancer or hepatocellular carcinoma (HCC) is an aggressive neoplasm that may not respond well to intravenous chemotherapy.

The choice of treatment for HCC normally depends on severity of underlying liver disease, size and number of lesions, location of lesions, ability to detect them with MRI, non-contrast CT, or ultrasound, and local expertise. Conventionally, physicians have employed RF ablation or microwave ablation to destroy the tumor tissue with heat, combined heating with coadministration of liposomes containing a drug, cryoablation to freeze a tumor, hepatic arterial drug infusion, bland arterial embolization, chemotherapy combined with arterial embolization, selective internal radioembolization using radioactive labeled iodized oil or radioactive microspheres as the embolic agent, external beam radiation therapy, or direct injection of an agent (e.g., ethanol, acetic acid, hot saline, or sodium hydroxide) to provide chemical toxic effects on the tumor tissue.

SUMMARY

Some thermochemical ablation techniques may provide minimally invasive ablation of tumors such as present with liver cancer, lung cancer, renal cancer, breast cancer, prostate cancer, sarcomas, or the like. These ablation techniques may induce chemical reactions to generate heat for ablation energy (e.g., employing chemical reaction energy rather than electrical energy, magnetic energy, or direct chemical toxic effects). Such chemical reactions may be induced by using a highly reactive electrophilic reagent such as acetic anhydride, ethyl chloroformate, malonyl chloride, acetyl chloride, or the like, and injecting the electrophilic reagent directly to the treatment location. The electrophile can react with nucleophiles present at the treatment site to produce heat and increase local temperature. For example, the nucleophiles present at the treatment site may either be weak nucleophiles inherent in the targeted tissue area (e.g., protein or carbohydrate molecules disposed on cell surfaces or the like), nucleophiles deposited at the treatment site (generally prior to electrophile injection), or a combination thereof. In addition to the substantial reaction heat generated locally at the targeted tissue site when the electrophile is injected (to ablate the targeted tissue), such ablation techniques can also provide a denaturing effect in which a localized residual acidic or basic/alcohol environment operates to inhibit tumor growth or cell production in the local area for a period of time after the electrophile injection. In these circumstances, the electrophile injection can generate significant ablation heat while still being a relatively small dosage, thereby reducing the overall acid load applied to the patient's system. Accordingly, the techniques described herein may permit a physician to treat multiple target locations in a single session.

In some embodiments, a thermochemical ablation system may include a percutaneous fluid delivery cannula comprising a first lumen extending from a proximal portion to a distal portion. The distal portion can include a first port in fluid communication with at least the first lumen. The system may also include a first reservoir containing a highly reactive electrophilic reagent in fluid communication with the first lumen of the percutaneous fluid delivery cannula. At least a portion of the highly reactive electrophilic reagent may be deliverable out of the first port to locally generate ablation heat at a targeted site and to provide a localized residual acidic environment at the targeted site for a period of time after generation of the ablation heat. The system may further include a real-time imaging system that monitors the distal portion of the percutaneous fluid delivery cannula and the delivery of the highly reactive electrophilic reagent, temperature monitoring, pH monitoring, or other monitoring or imaging system.

Particular embodiments include a method for thermochemical ablation of targeted tissue. The method may include delivering a highly reactive electrophilic reagent through a lumen of a percutaneous injection needle to a targeted tissue site. The method may also include reacting the delivered electrophilic reagent with nucleophiles at the targeted tissue location to locally generate ablation heat at the targeted tissue site and to provide a localized residual environment at the targeted tissue site for a period of time after generation of the ablation heat.

Some or all of these embodiments may provide one or more of the following advantages. First, the thermochemical ablation techniques may provide minimally invasive ablation of solid tumors such as liver cancer, lung cancer, renal cancer, breast cancer, prostate cancer, sarcomas, or the like. Such techniques may be useful, for example, to treat patients who are not surgical candidates due to the nature of the tumors or other intervening factors. Second, the thermochemical ablation techniques may induce chemical reactions to locally generate heat either to be the primary ablation source or to augment another ablation source (e.g., RF ablation, microwave ablation, or the like). Third, the chemical reactions may provide an inhibition effect of a residual acidic environment at the treatment location, further assisting in treatment. Fourth, some of the systems and devices described herein may be manufactured without high-cost components such as RF ablation probes, generators, or other ancillary equipment. Fifth, the thermochemical ablation techniques described herein may be used to treat larger tumors in a lower number of treatment sessions, thereby adding convenience to the patient. Sixth, the thermochemical ablation process can be monitored in real-time using medical imaging systems, such as ultrasound imaging devices or MRI systems. Seventh, the treatment regime does not require pre-heating, pre-mixing, or other chemical preparation prior to treatment, as the chemical action and ablation heat generation occurs locally at the targeted treatment site. Eighth, the delivery cannula may include a number of side ports that provide radial dispersion of the reagent when exiting the cannula, thereby distributing the ablation heat energy in a more even manner. Ninth, the locality of treatment may enable treatment of multiple locations in a single session. Tenth, there is no need for insulation of the needle shaft during injections, which makes a smaller outside diameter possible, with a corresponding reduction in trauma during treatment.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

A thermochemical ablation system may employ minimally invasive techniques to ablate solid tumors or other targeted tissue. These ablation techniques may induce chemical reactions to generate heat for ablation energy. Such chemical reactions may be induced by dispensing a highly reactive electrophile at a target treatment location. The highly reactive electrophile may react with nucleophiles inherently present at the treatment location (such as proteins, carbohydrates, or other organic nucleophiles occurring in the treatment tissue), or by reacting with nucleophiles added to the target treatment location such as by pre-treating the target location. Such a reaction can be used to locally generate substantial heat in the targeted tissue—heat that is sufficient to ablate the tissue (e.g., tumors or other tissues). Also, such ablation techniques can also provide a denaturing effect in which a localized residual environment operates to inhibit tumor growth or cell production in the local area for a period of time after the electrophile injection, thereby adding to the efficacy of treatment. For example, there may be a localized acidic environment following treatment using some chemical reagents. As another example, using different treatment reagents, there may be a residual basic and alcoholic environment. Either type of these residual environments will inhibit cell or tumor growth in the treatment area following treatment.

The thermochemical ablation techniques described herein can be used to treat solid tumors that arise in number of circumstances, including liver cancer, lung cancer, renal cancer, breast cancer, prostate cancer, sarcomas, or the like. These techniques may be useful, for example, to treat patients who are not surgical candidates due to the nature of the tumors or other intervening factors. For example, some patients with HCC or other types of liver cancer are not candidates for surgery. The thermochemical ablation system described herein may be effective in the treatment of such liver cancer in a manner that is relatively convenient to the patient (e.g., possibly reducing the number of treatment sessions) and relatively cost-effective for the medical care provider (e.g., not necessarily requiring high-cost equipment such as RF ablation probes, generator, or other ancillary equipment, and the like).

The described techniques may be used in percutaneous treatments. They may also be used as a treatment during open surgery, for example, as a method of intra-operative ablation.

Figure 1:
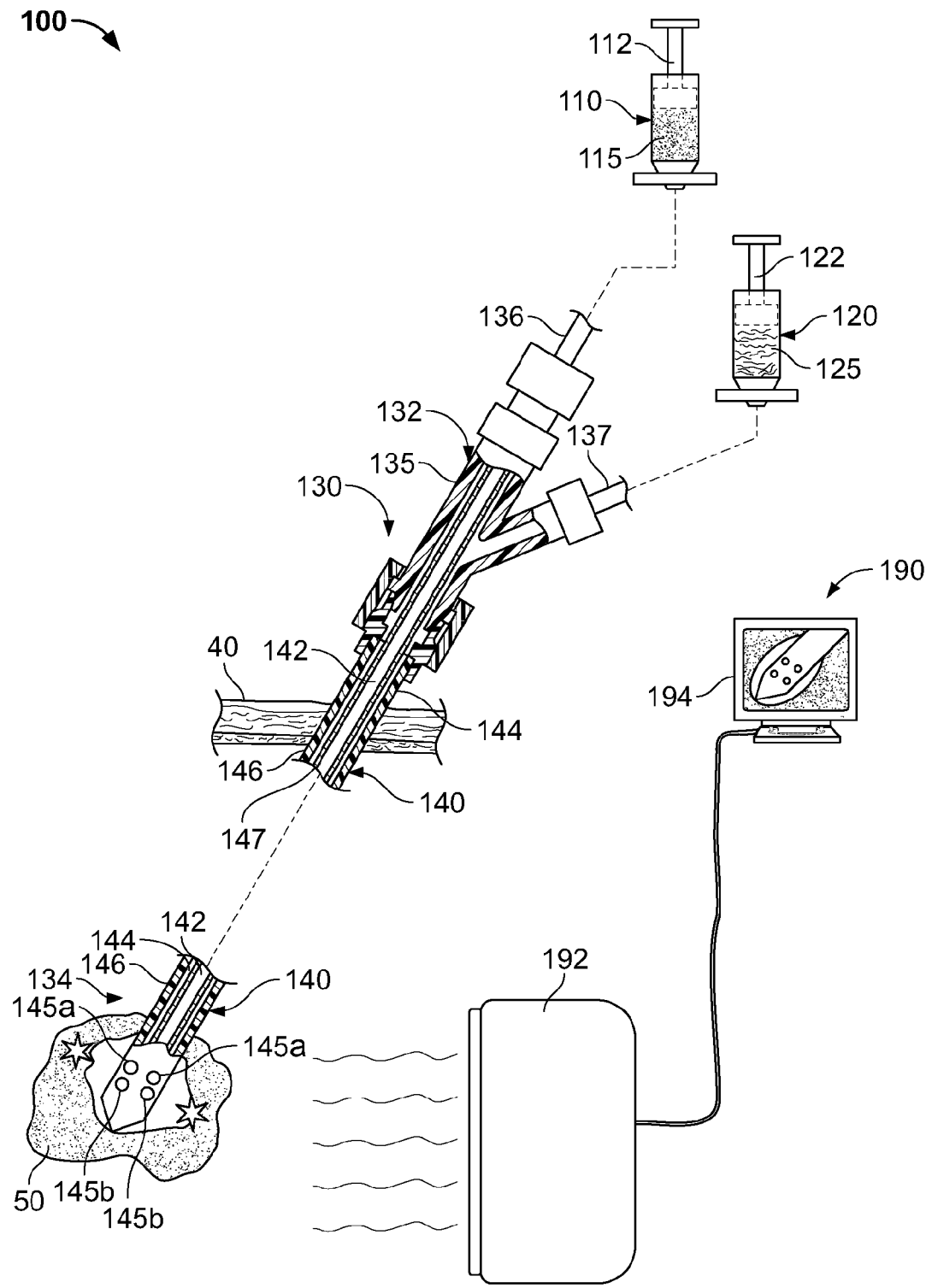
FIG. 1 is a section view of a thermochemical ablation system, in accordance with some embodiments.

Referring to FIG. 1, a thermochemical ablation system 100 is capable of infusing a highly reactive electrophile thermochemical ablation reagent into targeted tissue 50 to induce a chemical reaction and thereby ablate the tissue 50. The system 100 includes an electrophile fluid reservoir 110 that is in fluid communication with a thermochemical ablation device 130. The reservoir 110 may be detachable from the thermochemical ablation device 130. The reservoir 110 includes an electrophilic reagent 115, which may comprise a highly reactive electrophilic reagent that is capable of locally generating substantial heat upon delivery into the targeted tissue. For example, the highly reactive electrophile can react with nucleophiles inherently present in the targeted tissue (such as proteins or other organic nucleophiles occurring in the tissue) or can react with nucleophiles added to pre-treat the targeted tissue.

In the embodiments in which the targeted tissue will be pre-treated with a nucleophile prior to delivery of the highly reactive electrophilic reagent 115, the system 100 may optionally include a nucleophile fluid reservoir 120 that may be placed in fluid communication with thermochemical ablation device 130. The reservoir 120 includes a nucleophile reagent 125. Each of the reservoirs 110 and 120 includes an actuator 112 and 122 that can be adjusted to provide a dispensing force to the reagents 115 and 125. Accordingly, the reservoirs 110 and 120 can be removably attached to the proximal end of the device 130 and actuated to deliver reagents 115 and 125 to a proximal portion 132 of the fluid delivery device 130, which then passes the reagent to a distal portion 134 of the device 130.

In various approaches, a user may manually apply a force to the reservoir 110, 120 to deliver the reagents 115, 125 to the device 130, or, in another approach, a physician or other user may selectively activate a computer-controlled mechanism that acts upon the reservoir 110, 120 to provide the actuating force. A computer-controlled mechanism may provide for accuracy in small doses, may provide for using a dosage profile, or may provide other effects for dosages of the reagents 115 and 125 delivered from the reservoirs 110 and 120. In one embodiment, both reservoirs 110, 120 may be simultaneously coupled to the device 130 for ease of use. Such an approach may be beneficial to reduce errors in dosages and to enable faster treatment when both nucleophile and electrophilic reagents are to be used. In another embodiment, (shown in FIG. 5 and discussed below), a single lumen may be used for passage of fluid to the treatment location.

Referring again to FIG. 1, the thermochemical ablation device 130 includes a multi-lumen cannula 140 that can separately infuse the reagents 115 and 125 into the targeted tissue 50 proximate the distal portion 134. In particular, the cannula 140 includes a first lumen 142 in fluid communication with the first reservoir 110 to deliver the highly reactive electrophilic reagent 115 to the distal portion 134. Also, the cannula 140 includes a second lumen 144 in fluid communication with the second reservoir 120 to deliver the nucleophile reagent 125 to the distal portion 134. The distal portion 134 of the cannula 140 may include a plurality of fluid ports 145a-b to radially disperse the reagents 115, 125 into the treatment location proximate the distal portion 134.

Still referring to FIG. 1, this embodiment of the fluid delivery device 130 includes a cannula 140 in the form of a percutaneous injection needle. For example, the cannula 140 may includes a generally rigid needle body 146 having an outer diameter of about 0.135 inches or less, about 0.120 inches to about 0.008 inches, and about 0.072 inches to about 0.028 inches. The needle body 146 may comprise stainless steel or another generally rigid material that is suitable for percutaneous insertion through the patient's skin 40. In other embodiments, for example, the needle may comprise a rigid plastic or ceramic material, or other metal such as titanium. The use of such materials may allow for real-time imaging using MRI or other imaging systems. The needle may include an echogenic coating to improve visibility using imaging systems. Furthermore, the distal tip portion of the cannula 140 may include a pointed tip so as to facilitate penetration through the skin 40 and toward the targeted tissue 50. The cannula 140 may also include an internal tube 147 that passes through the needle body 146. In this embodiment, the internal tube 147 comprises a second, smaller needle body that is generally coaxial with the outer needle body 146, thereby defining the first lumen 142 within the second lumen 144. It should be understood that, in other embodiments, the first and second lumens 142 and 144 may be configured to have a side-by-side arrangement (refer, for example, to FIG. 3). In such circumstances, the first and second lumens 142 and 144 may be defined by two bores that are formed through the outer needle body 146 (e.g., without using a centrally located internal tube 147).

In some embodiments, the fluid delivery device 130 may be packaged as part of a thermochemical ablation kit, which the physician or other user can use without the need to further assemble any components of the device 130. For example, the fluid delivery device 130 may be manufactured so that outer needle body 146, the inner tube 147, and a valve device 135 are fully assembled and packaged into the kit. Also, the cannula 140 can be manufactured so that the first lumen 142 is in fluid communication with side ports 145a and the second lumen 144 is in fluid communication with the side ports 145b (described in more detail below, for example, in connection with FIGS. 2-4). In these circumstances, the physician or other user can readily unpackage the fluid delivery device 130 from the kit and thereafter connect both the first fluid line 136 of the fluid delivery device 130 to the first reservoir 110 and the second fluid line 137 to the second reservoir 120. Such fluid line connections permit the first and second reservoirs 110 and 120 to be in fluid communication with the first and second lumens 142 and 144.

As shown in FIG. 1, the distal portion 134 of the fluid delivery device 130 may include one or more side ports 145a-b through which the first and second reagents 115 and 125 are dispensed into the targeted tissue 50. The side ports 145a-b may be oriented so that the reagents 115 and 125 are radially dispersed from the distal portion 134. Such radial dispersion of the reagents may provide improved treatment of the target location by improved reagent distribution. Furthermore, the radial dispersion through the side ports can provide better localization of the reagents as they are dispersed radially, rather than a single axial stream.

The first set of side ports 145a may be in fluid communication with the first lumen 142 so that the reagent 115 is dispensed from the side ports 145a when the actuator 112 is adjusted. Likewise, the second set of side ports 145b may be in fluid communication with the second lumen 144 so that the reagent 125 is dispensed from the side ports 145b when the actuator 122 is adjusted. Accordingly, the fluid delivery device 130 provides for separate infusion of the reagents 115 and 125 into the targeted tissue 50, such that the highly reactive electrophilic reagent 115 may be dispersed at the target location to cause an exothermic chemical reaction. In some cases, the reaction may be primarily with, or supplemented by, reacting the electrophilic reagent 115 with the nucleophile reagent 125 that was previously dispersed at the target location.

The heat generated from this chemical reaction may be sufficient to ablate at least a portion of the targeted tissue 50 surrounding the distal portion 134 of the fluid delivery device 130. Because the fluid delivery device 130 infuses a highly reactive electrophilic reagent that chemically react with nucleophiles (rather than direct injection of a single acidic reagent), the byproducts of the chemical reaction may include greater heat generation with lower acid toxicity. However, the use of the electrophile reaction may still result in a localized environment that may inhibit cell growth in the target location. Accordingly, the thermochemical ablation techniques described herein may be used to treat tumors in fewer sessions with fewer complications from acid load toxicity.

The highly reactive electrophilic reagent 115 that is infused into the targeted tissue 50 may be selected to provide a suitable energy deposition in tissue and to provide other features, such as residual acidity. In some embodiments, the optional nucleophile reagent 125 may be selected to assist in treatment by increasing the temperature rise of the treatment location, by providing for greater distribution across a treatment area, or other effects. For example, the highly reactive electrophilic reagent 115 may comprise an electrophile selected from the group consisting of acetic anhydride, acetyl chloride, acetyl bromide, carboxylic acid anhydrides, other anhydrides, other acid halides, sulfonyl or phosphonyl anhydrides and halides (such as $SOCl_2$, $POCl_3$, $PCl_3$, etc), inorganic acid halides, chloroformates, chlorides, and the like. Specific examples of highly reactive electrophiles include acetic anhydride, ethyl chloroformate, malonyl chloride, and acetyl chloride. The electrophile may also include diagnostic groups (e.g., detectable on imaging systems). The electrophile may have various leaving groups that could include a diagnostic (such as bromide or iodide which would be more radio-opaque as a marker). The leaving group may also have better electron withdrawing capability (such as CF3, nitro groups, sulfonyl groups, halides, etc.) which would produce greater chemical reactivity due to the more electrophilic leaving group species. The optional nucleophile reagent 125 may comprise a nucleophile selected from the group consisting of alkoxides, thio analogues, mercaptans (e.g., sulfhydryl), some amines, bases, and the like. Examples of bases that may be used include bases selected from the group consisting of KOH, NaOH, $NH_4OH$, $Ca(OH)_2$, $NaHCO_3$, $K_2CO_2$, BuLi, NaOEt or NaSEt (e.g., Na or K salts of alkoxides or thio analogues), NaH, KH, particular amines, and the like. In some embodiments, either or both of the reagents could be chosen to have useful imaging or other analyzable features (e.g., fluorescence, nuclear isotopes, MR imaging characteristics, or the like) to permit a physician to evaluate the reagent distribution in the targeted tissue 50 and throughout the body.

As previously described, the particular electrophile and the optional nucleophile may be selected to product the desired heat generation and low toxicity byproducts. For example, in some embodiments, the highly reactive electrophilic reagent 115 may be either acetic anhydride or acetyl chloride, and the nucleophile reagent 125 may be NaOH, KOH, or NH4OH. Accordingly, the fluid delivery device 130 maintains the reagents in separate lumens, such that the nucleophile reagent 125 may be injected and infused at the targeted tissue 50 first. After this injection, the highly reactive electrophilic reagent 115 may be injected and infused at the target tissue 50 to react with the pre-treated reagent 125, as well as other nucleophiles present in the target tissue 50.

The pre-infusion of the nucleophile reagent can reduce the resulting acid load applied to the patient during the treatment, thereby alleviating some issues associated with acid load toxicity. The byproducts from the chemical reaction of the reagents 115 and 125 may further benefit the ablation process, for example, due to the hyperosmolarity of the environment, chaotropic properties as in the Hofmeister series of cations and anions, or other denaturing conditions.

Carrier fluids may also be used with either or both of the electrophilic and nucleophilic reagents. Various solvents that are non-reactive with the electrophiles or nucleophiles are preferred. Examples of suitable solvents include diglyme and polyether solvents. These solvents are nontoxic, readily available, clear and colorless, liquid, water-miscible, nonreactive with electrophiles & nucleophiles, and have a high enough boiling point to be useful and safe regarding vapors/evaporation. Water and other polar solvents are not preferred for use as a carrier with the electrophilic reagent, as the electrophilic reagent will react with water and in addition, there may be optimum concentrations for the reaction that are unsuitable for use with water as a carrier for other reasons such as dilution levels, etc.

Still referring to FIG. 1, some embodiments of the thermochemical ablation system 100 may include a medical imaging system that provides real-time monitoring of the device 130 insertion and the delivery of the reagent 115. For example, the medical imaging system can include an ultrasound imaging system 190 to enable a physician or other user to view the distal portion 134 of the fluid delivery device 130 in the targeted tissue 50. In this embodiment, the ultrasound imaging system 190 includes an ultrasound probe device 192 that can be manipulated on the outside of the patient's body or within a body cavity. The ultrasound probe 192 may be connected to an ultrasound display system 194 that interprets the signals from the probe 192 and generates a display of the targeted portion of the patient's body. For example, as shown in FIG. 1, the ultrasound display system 194 may show the distal portion 134 of the device 130 as it is inserted into the targeted tissue 50 for delivery of the thermochemical ablation reagents 115 or 125. It should be understood that, in other embodiments, the imaging system may comprise another type of system other than the ultrasound imaging system 190. For example, the medical imaging system may include a CT imaging system, MRI imaging system, or the like. Some or the entire delivery device 130 may comprise materials that are compatible with the selected imaging system so as to enable monitoring of the delivery device 130 during insertion. For example, the cannula 140 may comprise a metallic material, or other material treated to be echogenic, that can be visualized using the ultrasound imaging system 190. In another example, the distal portion 134 of the delivery device 130 may include magnetic resonance markers or other features that permit viewability using the selected imaging system. Furthermore, in some embodiments, the delivery device 130 may include depth markers that are directly viewable to the physician or other user. For example, the cannula 140 may include a number of depth markers on the outer surface of the needle body 146. The physician or other user can view these depth markers during insertion of the cannula 140 through the skin 40 to indicate the approximate depth of insertion.

Figure 2:
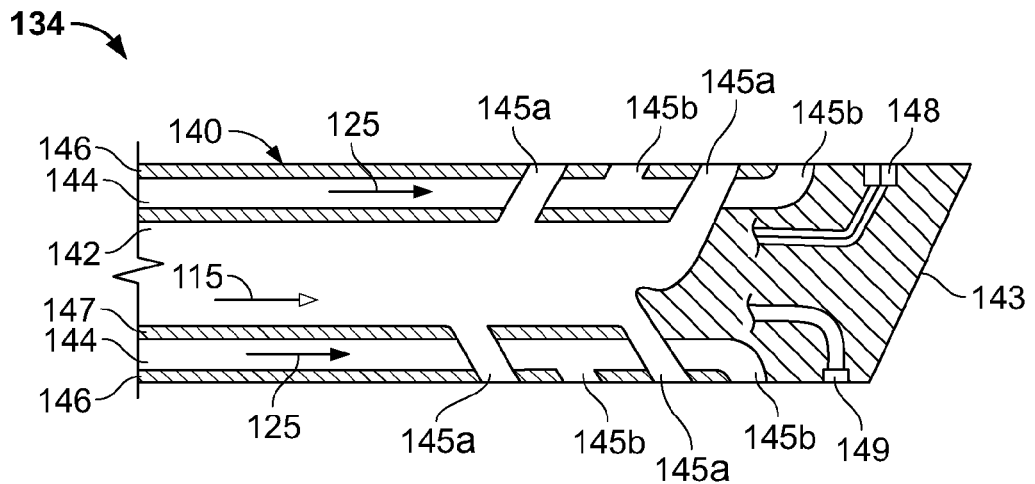
FIG. 2 is a cross-sectional view of a portion of a delivery cannula for a thermochemical ablation system, in accordance with some embodiments.

Referring to FIG. 2, the distal portion 134 of the fluid delivery device 130 may include one or more side ports 145a-b in the cannula 140. As previously described, the side ports 145a-b can be used to radially disperse the reagents 115 and 125 in the region proximate the distal portion 134. Such radial dispersion of the reagents can improve the distribution of the reagents 115 and 125. The first and second lumens 142 and 144 maintain the reagents 115 and 125 separate from one another until dispensed from the ports, after which the reagents are capable of generating an exothermic chemical reaction for ablating the targeted tissue.

It should be understood that, in other embodiments, the number of first side ports 145a and second side ports 145b may be different than that depicted in FIG. 2. For example, the cannula 140 may include only one first side port 145a and only one second side port 145b. In another example, the cannula 140 may include three, four, five, six, seven, eight, nine, ten, or more of the first side ports 145a. Also, the cannula 140 may include three, four, five, six, seven, eight, nine, ten, or more of the second side ports 145b. Furthermore, in some embodiments, the number of first side ports 145a may be different from the number of second side ports 145b. For example, the cannula 140 may include three of the first side ports 145a and four, five, or six of the second side ports 145b.

In this embodiment depicted in FIG. 2, the first lumen 142 is arranged coaxial with the second lumen 144. For example, the internal tube 147 may be disposed within the needle body 146 of the cannula 140 so as to define at least a portion of the first lumen 142 within the internal tube 147 and to define at least a portion of the second lumen 144 between the internal tube 147 and the needle body 146. The internal tube 147 may comprise a generally rigid material, such as stainless steel or the like. Alternatively, the internal tube may comprise a nonmetallic material (e.g., biocompatible polymer) that is assembled into the generally rigid needle body 146. It should be understood that, in other embodiments, the first and second lumens 142 and 144 may be arranged in the cannula 140 in a manner other than coaxial. For example, the first and second lumens 142 and 144 may be arranged in a side-by-side configuration (refer, for example, the embodiment described in connection with FIG. 3).

Still referring to FIG. 2, the first lumen 142 is in fluid communication with the first set of side ports 145a such that the electrophilic reagent 115 can be delivered through the first lumen 142 and out through the side ports 145a. Also, the second lumen 144 is in fluid communication with the second set of side ports 145b such that the nucleophile reagent 125 can be delivered through the second lumen 144 and out through the side ports 145b. The walls that at least partially define the first and second lumens (e.g., in this embodiment, the needle body 146 and the internal tube 147) are configured to maintain the reagents 115 and 125 separate from one another.

In this embodiment, the cannula 140 includes a closed distal end 143. As such, the thermochemical ablation reagents 115 and 125 are dispensed from the side ports 145a-b rather than from end ports in the distal end 143. In some embodiments, the distal end may be formed with one or more end ports, and those end ports are plugged or otherwise sealed to ensure that the thermochemical ablation reagents 115 and 125 are dispensed only from the side ports 145a-b. As previously described, the side ports 145a-b can be used to radially disperse the first and second thermochemical ablation reagents 115 and 125, which can improve the distribution of the reagents 115 and 125 and can more evenly distribute the heat generated by the reaction.

Still referring to FIG. 2, some embodiments of the fluid delivery device 130 may include one or more sensors arranged on the distal portion 134. For example, in this embodiment, the distal portion 134 includes at least one temperature sensor 148 disposed at or near an outer surface of the cannula 140. The temperature sensor 148 may comprise a thermocouple instrument, such as a type K thermocouple, that has leads incorporated into the body of the cannula 140 (e.g., electrical lines embedded into the walls, insulated electrical traces formed on an inner or outer wall, or the like). The leads may extend from the temperature sensor 148 back to the proximal portion 132 (FIG. 1) of the fluid delivery device 130 so as to connect with a sensor computer system (not shown in FIGS. 1-2). The sensor computer system may be configured to indicate a temperature of the tissue disposed near the temperature sensor 148 based upon signals communicated from the temperature sensor 148. Such temperature information may be used, for example, by a physician or other user during the procedure to monitor the ablation of the targeted tissue.

In another example of a sensor, the distal portion 134 of the delivery device 130 may include at least one pH sensor 149 arranged disposed proximate an outer surface of the cannula 140. The pH sensor 149 may comprise a pH probe instrument that has an electrical lead incorporated into the body of the cannula 140 (e.g., electrical lines embedded into the walls, insulated electrical traces formed on an inner or outer wall, or the like). The lead may extend from the pH sensor 149 back to the proximal portion 132 (FIG. 1) of the fluid delivery device 130 so as to connect with a sensor computer system (not shown in FIGS. 1-2). The sensor computer system may be configured to indicate a pH level of the material proximate the distal portion based upon signals communicated from the pH sensor 149. Such pH information may be used, for example, by a physician or other user during the procedure to monitor the acid load applied to the tissue.

Other examples of sensors include an MR compatible sensor such as a fluoroptic probe, echogenic probes or probes with echogenic coatings for use with ultrasound equipment, etc. These probes may assist with visualization and location during procedures and treatment.

Figure 3:
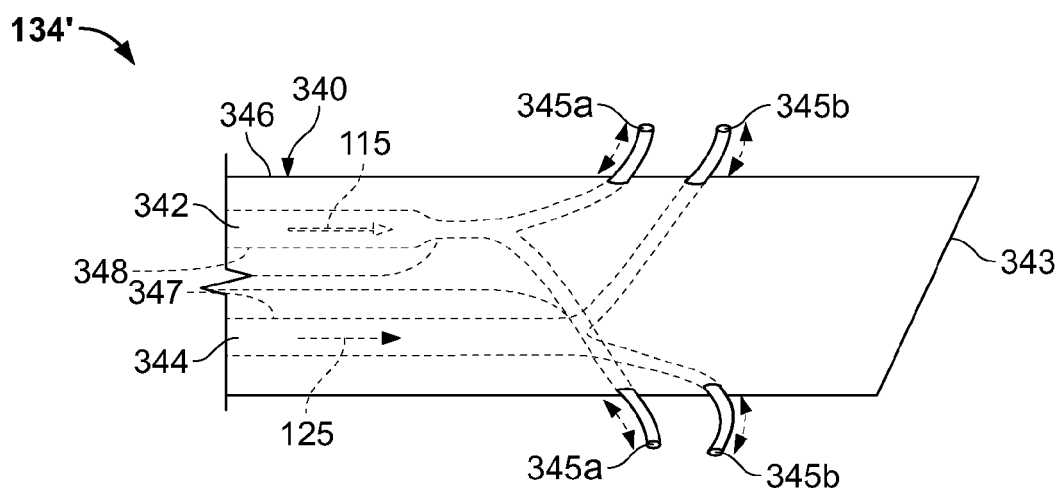
FIG. 3 is a cross-sectional view of a portion of yet another alternative delivery cannula for a thermochemical ablation system, in accordance with some embodiments.

Referring now to FIG. 3, some embodiments of the fluid delivery device may include a multi-lumen cannula in which at least one lumen is not arranged in a coaxial configuration. Furthermore, some embodiments of the fluid delivery device may include a cannula with adjustable side projections that dispense the thermochemical ablation reagents 115 and 125. FIG. 3 is used to illustrate both of these embodiments at once, though they may be separately implemented.

In the embodiment shown in FIG. 3, an alternative distal portion 134' of the fluid delivery device includes a cannula 340 having at least two lumens 342 and 344 in a non-coaxial configuration, and which can be adjusted relative to an outer needle body 346. The first lumen 342 is arranged adjacent to the second lumen 344. For example, the first and second lumens 342 and 344 may be at least partially defined by two adjacent bores formed through the cannula 340. In such circumstances, the cannula 340 may comprise a generally rigid needle body 346 in which the first and second lumens 342 and 344 are formed and thereby separated by an intermediate wall portion. Furthermore, the first lumen 342 may be at least partially defined by a first tube 348 that can be actuated from a proximal position to a distal position so that first side projections 345a protrude outwardly from the radial surface of the cannula 340. Similarly, the second lumen 344 may be at least partially defined by a second tube 347 that can be actuated from a proximal position to a distal position so that second side projections 345b protrude outwardly from the radial surface of the cannula 340. The first and second side projections 345a-b may include ports therein that dispense the first and second thermochemical ablation reagents 115 and 125 from the projections. Accordingly, the first and second side projections 345a-b can be adjusted from a retracted position (e.g., a position generally within a bore of the outer needle body 346) to an extended position (e.g., refer to FIG. 4) so as to penetrate into a wider region of the targeted tissue and further distribute the thermochemical ablation energy during delivery of the reagents 115 and 125.

In this embodiment, the outer needle body 346 comprises a generally rigid material (e.g., stainless steel or the like) and the first and second tubes 348 and 347 comprise a shape memory alloy that exhibits superelastic characteristics when inside the patient's body. For example, the first and second tubes 348 and 347 may comprise nitinol material or the like, which provides superelastic flexibility during the transition from the retracted position (e.g., the side projections 345a-b are constrained generally within a bore of the outer needle body 346) to the extended position. As such, the side projections 345a-b may have a curved shape or other configuration that permits the ports of the side projections to be pointed toward particular regions.

In use, a physician or other user can direct the distal portion 134' to the targeted tissue under guidance from a medical imaging system 190 (FIG. 1). In such circumstances, the side projections 345a-b may be in the retracted position to facilitate insertion of the cannula 340 into the patient. When the targeted tissue is reached by the distal portion 134', the physician or other user may operate a trigger device or other actuator (not shown in FIG. 3) that causes the first and second tubes 348 and 347 to shift positions relative to the outer needle body 346. For example, the trigger device may cause the first and second tubes 348 and 347 to adjust distally, thereby forcing the side projections 345a-b to the extended position radially outward of the cannula 340. As such, the side projections 345a-b act as tines that penetrate into a wider region of the targeted tissue. Thereafter, the physician or other user can act to dispense the reagents 115 and 125 out of the ports in the side projections 345a-b.

It should be understood that, in some embodiments, the cannula 340 may have lumens 342 and 344 that are arranged in a coaxial configuration, in a side-by-side configuration, or in a different configuration. Also, in some embodiments, the cannula 340 may have a number of side ports to dispense the reagents directly from the cannula 340 (in addition to the fluid delivery from the side projections 345a-b). Further, in some embodiments, the cannula 340 may have a closed distal end 343 similar to that described in connection with FIG. 2. In particular embodiments, the distal portion 134' of the fluid delivery device may include one or more sensors arranged on the cannula 340. For example, the cannula 340 may incorporate a temperature sensor (e.g., sensor 148 described in connection with FIG. 2), a pH sensor (e.g., sensor 149 described in connection with FIG. 2), or the like. Such sensors may provide useful information to the physician or other user during the ablation procedure.

Figure 4:
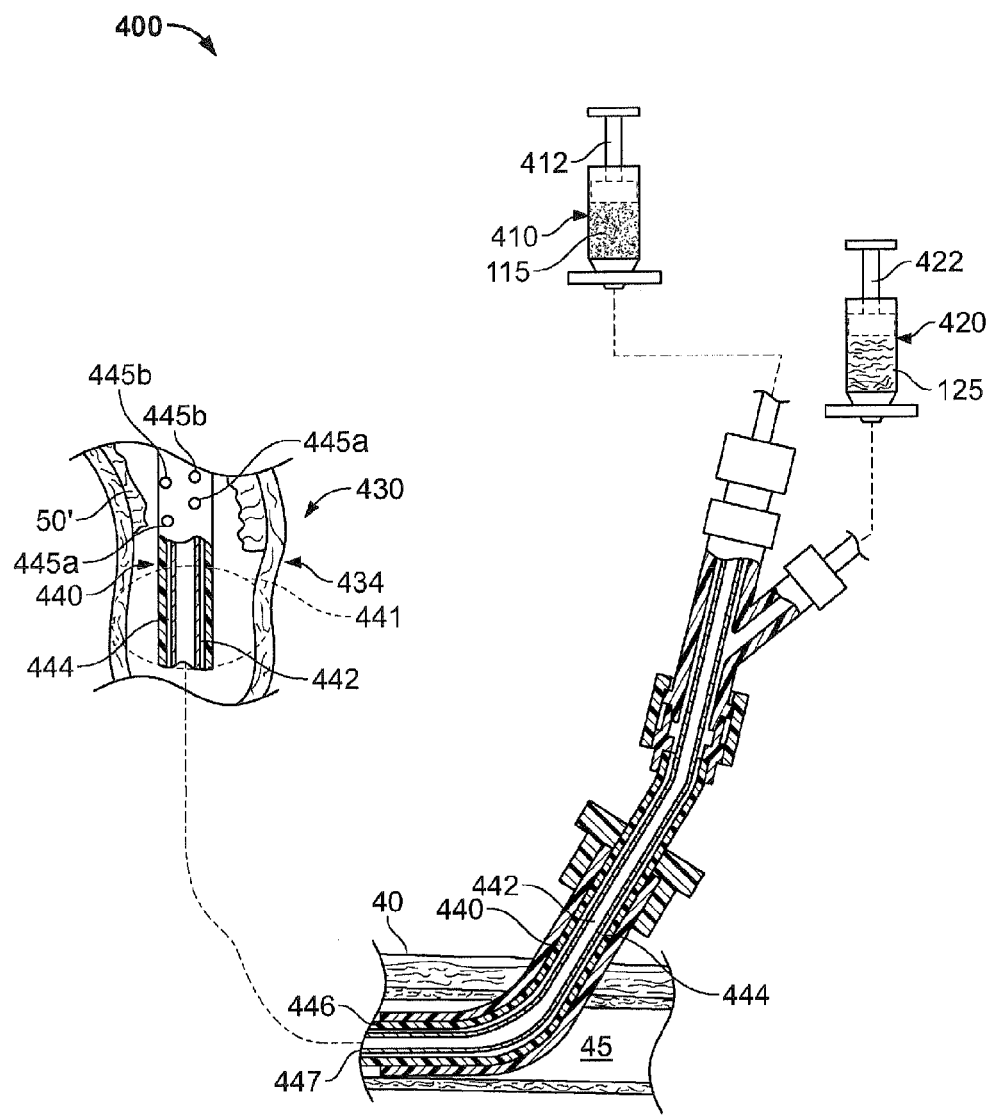
FIG. 4 is a section view of an alternative embodiment of a thermochemical ablation system.

Referring now to FIG. 4, some embodiments of a thermochemical ablation system 400 may include a fluid delivery device 430 having a cannula 440 that is at least partially flexible. For example, the cannula 440 may comprise a flexible catheter body 446 that is deliverable through a bodily passageway 45, including a vein, an artery, a urethra, a rectum, a vagina, an esophagus, ureter, bile duct, uterus, or the like. Accordingly, a physician or other user can direct a distal portion 434 of the fluid delivery device 430 through the bodily passageway 45 and toward a targeted tissue 50' (e.g., a tumor, a vasculature occlusion, a urethral occlusion, or the like) for ablation or other treatment of the targeted tissue 50'.

Similar to previously described embodiments, the thermochemical ablation system 400 includes a first fluid reservoir 410 and a second fluid reservoir 420 that are in fluid communication with the thermochemical ablation device 430. The first reservoir 410 includes the highly reactive electrophilic reagent 115, and the second reservoir 420 includes the optional nucleophile reagent 125. Each of the reservoirs 410 and 420 includes an actuator 412 and 422 that can be adjusted to provide a dispensing force to the reagents 115 and 125.

Similar to previously described embodiments, the cannula 440 of the fluid delivery device 430 includes a first lumen 442 in fluid communication with the first reservoir 410 and a second lumen 444 in fluid communication with the second reservoir 420. Also, the distal portion 434 of the delivery device 430 may include a plurality of fluid ports 445a-b to disperse the reagents 115 and 125 in the region proximate the distal portion 434. The relationship of the reagents to the lumens is not critical, and either reagent could be dispensed through either lumen, depending upon various configurations and preferences.

This embodiment of the fluid delivery device 430 includes the cannula 440 in the form of a flexible catheter device. For example, the cannula 440 may include a generally flexible catheter body 446 comprised of a biocompatible polymer. The fluid delivery device 430 may include a steering mechanism (e.g., steering wires, shape memory actuators, or the like) so that the distal tip of the cannula 440 can be navigated through the bodily passageway 45. The cannula 440 may also include an internal tube 447 that is formed inside the catheter body 446. As such, the first lumen 442 is at least partially defined by the internal tube 447, and the second lumen 444 is at least partially defined between the catheter body 446 and the internal tube 447. Thus, in this embodiment, the first and second lumens 442 and 444 are arranged in a coaxial configuration. In other embodiments, the first and second lumens 442 and 444 can be arranged in a side-by-side configuration or in other configurations.

The distal portion 434 of the fluid delivery device 430 may include one or more side ports 445a-b through which the first and second reagents 115 and 125 are dispensed into the targeted tissue 50'. The side ports 445a-b may be oriented so that the reagents 115 and 125 are radially dispersed from the distal portion 434. Such radial dispersion of the thermochemical ablation reagents may provide improved treatment of the target treatment location, as the radial dispersion through the side ports 445a-b can more evenly distribute the reagents to better distribute the heat generated by the reaction. It should be understood that, in some embodiments, the cannula 440 may have a closed distal end similar to that described in connection with FIG. 2 or end ports similar to those described in connection with FIG. 3. Also, in alternative embodiments, the cannula 440 may include end ports without any side ports 445a-b. In particular embodiments, the distal portion 434 of the fluid delivery device 430 may include one or more sensors arranged on the cannula 440. For example, the cannula 440 may incorporate a temperature sensor (e.g., sensor 148 described in connection with FIG. 2), a pH sensor (e.g., sensor 149 described in connection with FIG. 2), or the like. Such sensors may provide useful information to the physician or other user during the ablation procedure.

As shown in FIG. 4, the first set of side ports 445a may be in fluid communication with the first lumen 442 so that the reagent 115 is dispensed from the side ports 445a when the actuator 412 is adjusted. Likewise, the second set of side ports 445b may be in fluid communication with the second lumen 444 so that the reagent 125 is dispensed from the side ports 445b when the actuator 422 is adjusted. Accordingly, the fluid delivery device 430 provides for sequential infusion of the reagents 115 and 125 into the targeted tissue 50'. The reaction of the highly reactive electrophilic reagent 115 is an exothermic chemical reaction, and the heat generated from the chemical reaction may be sufficient to ablate at least a portion of the targeted tissue 50' surrounding the distal portion 434 of the fluid delivery device 430. As previously described, pretreating the targeted tissue 50' with nucleophile reagent 125 may result in greater heat generation with lower acid load toxicity. It should be understood that, in some embodiments, there is no pre-loading or use of an external nucleophile, and the reaction only includes reaction of already present nucleophiles at the target tissue 50' upon addition of the highly reactive electrophilic reagent 115.

Still referring to FIG. 4, the fluid delivery device 430 may optionally include an expandable balloon device 441 disposed along the distal portion 434. The expandable balloon device 441 may be used to anchor the distal tip of the cannula 440 in a desired location within the bodily passage way 45. Alternatively, the expandable balloon may be used to temporarily seal the bodily passageway 45 during the delivery of the reagents 115 and 125 from the catheter body 446. For example, the balloon 441 may be filled with saline or another fluid to press against the wall of a vein or artery, thereby temporarily hindering blood flow through that portion of the vein or artery. The reagents 115 and 125 can be dispensed as previously described while the balloon 441 is expanded, which permits the highly reactive electrophilic reagent 115 to remain near the target tissue 50' without being carried away by ordinary blood flow. After the ablation procedure is completed, the balloon may be collapsed for removal of the fluid delivery device 430.

Some embodiments of the thermochemical ablation system 400 may include a medical imaging system that provides real-time monitoring of device 430 insertion and the delivery of the reagents. For example, the medical imaging system can include an ultrasound imaging system 190 (refer, for example, to FIG. 1) to enable a physician or other user to view the distal portion 434 of the fluid delivery device 430 in the targeted tissue 50'. In another example, the medical imaging system may include a CT imaging system, MRI system, or the like. The delivery device 430 may comprise one or more materials that are compatible with the selected imaging system so as to enable monitoring of the delivery device 430 during insertion. For example, the cannula 440 may comprise a metallic material that can be visualized using the ultrasound imaging system 190. In another example, the catheter body 446 of the cannula 440 may include magnetic resonance markers inserted therein which provide viewability using the selected imaging system. Furthermore, in some embodiments, the delivery device 430 may include depth markers that are directly viewable to the physician or other user. For example, the outer catheter body 446 may include a number of depth markers. The physician or other user can view these depth markers during insertion of the cannula 440 through the skin 40 to indicate the approximate depth of insertion. Accordingly, a physician or other user can direct a distal portion 434 of the fluid delivery device 430 through the bodily passageway 45 and toward a targeted tissue 50' (e.g., a tumor, a vasculature occlusion, a urethral occlusion, or the like) for ablation or other treatment of the targeted tissue 50'.

Figure 5:
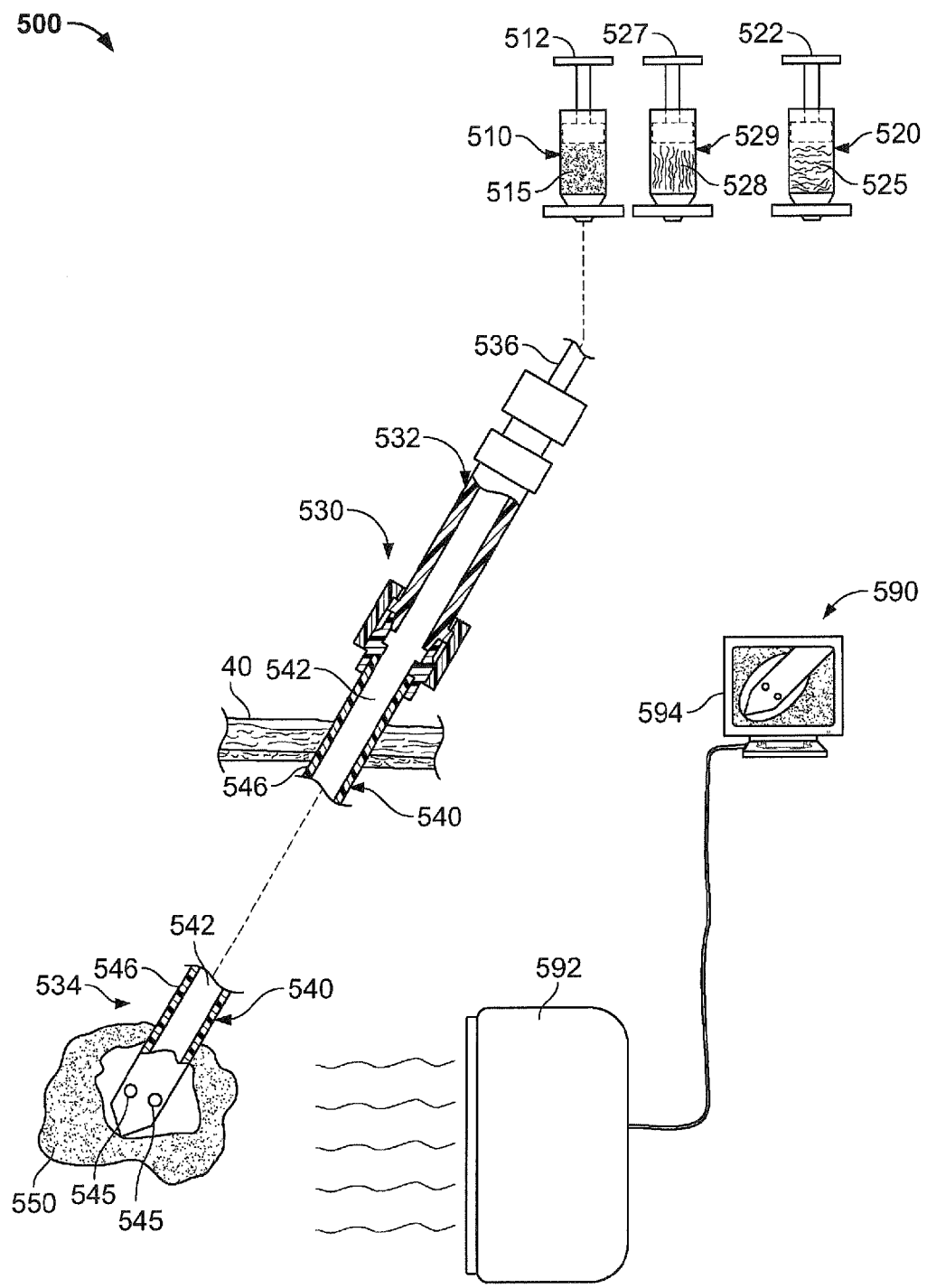
FIG. 5 is a section view of an alternative embodiment of a thermochemical ablation system.

Referring to FIG. 5, a thermochemical ablation system 500 is capable of infusing a highly reactive electrophile thermochemical ablation reagent into targeted tissue 550 to induce a chemical reaction and thereby ablate the tissue 550. The system 500 includes an electrophile fluid reservoir 510 that is in fluid communication with a thermochemical ablation device 530. The reservoir 510 may be detachable from the thermochemical ablation device 530. The reservoir 510 includes a highly reactive electrophilic reagent 515. The reservoir 510 includes an actuator 512 that can be adjusted to provide a dispensing force to the reagent 515. Accordingly, the reservoir 510 can be attached to the proximal end of the device 530 and actuated to deliver reagent 515 to a proximal portion 532 of the fluid delivery device 530, which then passes the reagent to a distal portion 534 of the device 530. In one approach, a user may manually apply a force to the reservoir 510 to deliver the reagent 515 to the device 530, or, in another approach, a physician or other user may selectively activate a computer-controlled mechanism that acts upon the reservoir 510 to provide the actuating force. A computer-controlled mechanism may provide for accuracy in small doses, may provide for using a dosage profile, or other effects for dosages of the reagent 515 delivered from the reservoir 510.

In one embodiment, the thermochemical ablation device 530 includes a cannula 540 that includes lumen 542 in fluid communication with the reservoir 510 to deliver the highly reactive electrophilic reagent 515 to the distal portion 534. The distal portion 534 of the cannula 540 may include a plurality of fluid ports 545 to radially disperse the reagent 515 into the treatment location 550 proximate the distal portion 534.

Still referring to FIG. 5, this embodiment of the fluid delivery device 530 includes a cannula 540 in the form of a percutaneous injection needle. For example, the cannula 540 may includes a generally rigid needle body 546 having an outer diameter of about 0.135 inches or less, about 0.120 inches to about 0.008 inches, and about 0.072 inches to about 0.028 inches. The needle body 546 may comprise stainless steel or another generally rigid material that is suitable for percutaneous insertion through the patient's skin 40. In other embodiment, the needle may comprise a rigid plastic or ceramic material, or other metal such as titanium. The use of such materials may allow for real-time imaging using MRI or other imaging systems. Furthermore, the distal tip portion of the cannula 540 may include a pointed tip so as to facilitate penetration through the skin 40 and toward the targeted tissue treatment location 550.

In some embodiments, the fluid delivery device 530 may be packaged as part of a thermochemical ablation kit, which the physician or other user can use without the need to further assemble any components of the device 530. In these circumstances, the physician or other user can readily unpackage the fluid delivery device 530 from the kit and thereafter connect the first fluid line 536 of the fluid delivery device 530 to the reservoir 510.

As shown in FIG. 5, the distal portion 534 of the fluid delivery device 530 may include one or more side ports 545 through which the reagent 515 is dispensed into the targeted tissue treatment location 550. Such radial dispersion of the reagents may provide improved treatment of the target location by improved reagent distribution. Furthermore, the radial dispersion through the side ports can provide better localization of the reagent as the reagent is dispersed radially, compared to injecting as a single axial stream.

Dispensing of the highly reactive electrophilic reagent 515 at the target treatment location 550 causing an exothermic reaction between the electrophilic reagent 515 and nucleophiles present at the targeted tissue (such as proteins or other naturally occurring nucleophiles present in the targeted tissue).

The heat that is locally generated from this chemical reaction may be sufficient to ablate at least a portion of the targeted tissue 550 surrounding the distal portion 534 of the fluid delivery device 530. Because the fluid delivery device 530 infuses a highly reactive electrophilic reagent that chemically reacts with nucleophiles, the byproducts of the chemical reaction may include greater heat generation with lower acid toxicity. However, the use of the electrophile reaction may result in a localized acidic environment that may inhibit cell growth in the target location. Accordingly, the thermochemical ablation techniques described herein may be used to treat tumors in fewer sessions with fewer complications from acid load toxicity.

The highly reactive electrophilic reagent 515 that is infused into the targeted tissue 550 may be selected to provide a suitable energy deposition in tissue and to provide other features, such as residual acidity. For example, the highly reactive electrophilic reagent 515 may comprise electrophiles such as discussed earlier. The reagent may also be selected to have useful imaging or other analyzable features (e.g., fluorescence, nuclear isotopes, MR imaging characteristics, or the like) to permit a physician to evaluate the reagent distribution in the targeted tissue 550.

Still referring to FIG. 5, some embodiments of the thermochemical ablation system 500 may include a medical imaging system that provides real-time monitoring of the device 530 insertion and the delivery of the reagent 515. For example, the medical imaging system may include an ultrasound imaging system 590 to enable a physician or other user to view the distal portion 534 of the fluid delivery device 530 in the targeted tissue 550. In this embodiment, the ultrasound imaging system 590 includes an ultrasound probe device 592 that can be manipulated on the outside of the patient's body or within a body cavity. The ultrasound probe 592 may be connected to an ultrasound display system 594 that interprets the signals from the probe 592 and generates a display of the targeted portion of the patient's body. For example, the ultrasound display system 594 may show the distal portion 534 of the device 530 as it is inserted into the targeted tissue 550. It should be understood that, in other embodiments, the imaging system may comprise another type of system other than the ultrasound imaging system 590. For example, the medical imaging system may include a CT imaging system, MRI imaging system, or the like. Some or the entire delivery device 530 may comprise materials that are compatible with the selected imaging system so as to enable monitoring of the delivery device 530 during insertion. For example, the cannula 540 may comprise a metallic material that can be visualized using the ultrasound imaging system 590. In another example, the distal portion 534 of the delivery device 530 may include magnetic resonance markers or other features that permit viewability using the selected imaging system. Furthermore, in some embodiments, the delivery device 530 may include depth markers that are directly viewable to the physician or other user. For example, the cannula 540 may include a number of depth markers on the outer surface of the needle body 546. The physician or other user can view these depth markers during insertion of the cannula 540 through the skin 40 to indicate the approximate depth of insertion.

The system 500 may optionally include additional reservoirs that may be removably attached to the delivery device 530. For example, a nucleophile fluid reservoir 520 may be placed in fluid communication with the delivery device 530. The reservoir 520 includes a nucleophile reagent 525. The nucleophile reagent 525 may be dispensed by activating actuator 522. The nucleophile may be used to pre-load the target location 550 with a nucleophile for reaction with the highly reactive electrophile. This may be beneficial for various reasons such as increasing the heat of reaction, reducing acid load, improving visualization, or to provide other beneficial effects. As another example, an inert reagent reservoir 529 may be placed in fluid communication with the delivery device 530. The reservoir 529 includes an inert reagent 528. The inert reagent 528 may be dispensed by activating actuator 527. The inert reagent may be used to separate the nucleophile from the electrophilic reagents in the delivery device 530, so that all reaction occurs at the target tissue location 550. The inert reagent may be beneficial for various other reasons such as improving the dispersion of reagents, improving visualization, or to provide other beneficial effects.

The thermochemical ablation systems described herein may be employed in minimally invasive techniques to ablate solid tumors or other targeted tissue. These ablation techniques may induce chemical reactions to generate heat for ablation energy. Such chemical reactions may be induced by mixing at least one acid reagent and at least one base reagent, which can neutralize or otherwise reduce the acid load applied to the patient during the procedure. Other reagents can be used to induce the desired exothermic chemical reaction. The thermochemical ablation techniques described herein can be used to treat solid tumors that arise in number of circumstances, including liver cancer, lung cancer, renal cancer, breast cancer, prostate cancer, sarcomas, or the like. Furthermore, the thermochemical ablation techniques described herein can be used to treat other targeted tissue, such as occlusions that arise in bodily passageways. Finally, the thermochemical ablation techniques described herein are not limited to use in human patients. For example, the thermochemical ablation systems described herein may be used to treat other animal patients, including mammalian patients.

EXAMPLES

Example 1

Acetic Anhydride

Acetic Anhydride was injected alone into porcine liver samples at volumes of 100, 200, 300, and 500 microliters. A total of 25 runs were conducted using Acetic Anhydride alone. Recorded temperature changes were quite variable using Acetic Anhydride and ranged from 0.0-2.94 degrees C. for all volumes injected. Using the thermocouple probe, it was determined that all volumes of Acetic Anhydride produced at least a 1.0 degree C. temperature change from baseline; however, the degree of temperature change did not correlate well with the overall volume of Acetic Anhydride used. Injections using 300 microliters appeared to produce the greatest and most predictable temperature changes with three out of five injections producing greater than one degree Celsius temperature change.

The inconsistency in these measurements is likely due to factors affecting the tissue distribution of the Acetic Anhydride rather than the overall volume of injected solution. The variability may be attributable to backflow through the injection site as well as a "conduit phenomenon". In this experiment, it was observed that large vessels provide pathways where Acetic Anhydride is allowed to travel through liver parenchyma to distant sites in the tissue where the thermocouple probe cannot record measurements. Based on visual observation of tissue destruction capacity, larger volumes of Acetic Anhydride correlated with greater areas of tissue destruction; however, the patterns of destruction were variable depending on the amount of backflow and conduit phenomenon observed for each injection series.

Results are reported below in Tables 1A-1E.

TABLE 1A

Acetic Anhydride alone: 100 microliters - different temp probe

| Time (Min) | Trial #1 Temp: C. | Trial #2 Temp: C. | Trial #3 Temp: C. | Trial #4 Temp: C. | Trial #5 Temp: C. |
| --- | --- | --- | --- | --- | --- |
| 0:00 | 17.9 | 17.6 | 17.7 | 17.7 | 17.6 |
| 0:15 | 17.9 | 18.1 | 18.2 | 18.2 | 18 |
| 0:30 | 17.9 | 18.1 | 18.2 | 18.2 | 18 |
| 0:45 | 17.9 | 18 | 18.2 | 18.2 | 18.3 |
| 1:00 | 17.9 | 18 | 18.3 | 18.3 | 18.2 |
| 1:15 | 17.9 | 18 | 18.3 | 18.3 | 18.2 |
| 1:30 | 17.9 | 18 | 18.3 | 18.3 | 18.2 |
| 1:45 | 17.9 | 18 | 18.3 | 18.3 | 18.1 |
| 2:00 | 17.9 | 17.9 | 18.3 | 18.3 | 18.1 |
| 2:15 | 17.9 | 17.9 | 18.3 | 18.3 | 18.1 |
| 2:30 | 17.9 | 17.9 | 18.3 | 18.3 | 18.1 |
| 2:45 | 17.9 | 17.9 | 18.3 | 18.3 | 18.1 |
| 3:00 | 17.9 | 17.9 | 18.1 | 18.1 | 18.1 |
| 3:15 | 17.9 | 17.9 | 18.1 | 18.1 | 18.1 |
| 3:30 | 17.9 | 17.9 | 18.1 | 18.1 | 18 |
| 3:45 | 17.9 | 17.9 | 18.1 | 18.1 | 18 |
| 4:00 | 17.9 | 17.9 | 18.1 | 18.1 | 18 |
| 4:15 | 17.9 | 17.9 | 18.1 | 18.1 | 18 |
| 4:30 | 17.9 | 17.9 | 18 | 18 | 18 |
| 4:45 | 17.9 | 17.9 | 18 | 18 | 18 |
| 5:00 | 17.9 | 17.9 | 18 | 18 | 18 |
| Changes | 0 | 0.5 | 0.6 | 0.6 | 0.7 |

TABLE 1B

Acetic Anhydride alone: 100 microliters

| | Trial #1 | | Trial #2 | | Trial #3 | | Trial #4 | | Trial #5 | |
| --- | --- | --- | --- | --- | --- | --- | --- | --- | --- | --- |
| Time (Min) | Temp: C. | pH | Temp: C. | pH | Temp: C. | pH | Temp: C. | pH | Temp: C. | pH |
| 0:00 | 21.3 | 7.52 | 19.2 | 7.1 | 19.7 | 6.14 | 19.3 | 6.23 | 19.6 | 6.33 |
| 0:15 | 21.4 | 3.75 | 20.3 | 3.34 | 19.9 | 5.7 | 19.5 | 6.03 | 19.8 | 5.2 |
| 0:30 | 21.5 | 3.54 | 20.3 | 3.2 | 20.4 | 5.63 | 19.5 | 6.01 | 19.8 | 5.06 |
| 0:45 | 21.6 | 3.43 | 20.4 | 3.11 | 20.5 | 5.54 | 19.5 | 5.92 | 19.8 | 4.9 |
| 1:00 | 21.6 | 3.36 | 20.5 | 3.05 | 20.6 | 5.42 | 19.5 | 5.91 | 19.8 | 4.81 |
| 1:15 | 21.6 | 3.27 | 20.5 | 2.98 | 20.6 | 5.25 | 19.5 | 5.87 | 19.8 | 4.75 |
| 1:30 | 21.6 | 3.2 | 20.5 | 2.9 | 20.6 | 5.05 | 19.5 | 5.82 | 19.8 | 4.6 |
| 1:45 | 21.6 | 3.12 | 20.5 | 2.84 | 20.6 | 4.45 | 19.6 | 5.72 | 19.7 | 4.55 |

TABLE 1B-continued

Acetic Anhydride alone: 100 microliters

| Time (Min) | Trial #1 Temp: C. | pH | Trial #2 Temp: C. | pH | Trial #3 Temp: C. | pH | Trial #4 Temp: C. | pH | Trial #5 Temp: C. | pH |
|---|---|---|---|---|---|---|---|---|---|---|
| 2:00 | 21.6 | 3.09 | 20.5 | 2.77 | 20.5 | 4.3 | 19.6 | 5.5 | 19.7 | 4.47 |
| 2:15 | 21.5 | 3.03 | 20.6 | 2.75 | 20.5 | 4.23 | 19.6 | 5.3 | 19.7 | 4.4 |
| 2:30 | 21.4 | 2.96 | 20.6 | 2.71 | 20.5 | 4.21 | 19.6 | 4.79 | 19.7 | 4.35 |
| 2:45 | 21.3 | 2.92 | 20.6 | 2.68 | 20.5 | 4.16 | 19.6 | 4.65 | 19.7 | 4.3 |
| 3:00 | 21.3 | 2.9 | 20.6 | 2.65 | 20.5 | 4.12 | 19.6 | 4.57 | 19.7 | 4.25 |
| 3:15 | 21.3 | 2.88 | 20.7 | 2.61 | 20.5 | 4.01 | 19.6 | 4.48 | 19.7 | 4.22 |
| 3:30 | 21.3 | 2.84 | 20.7 | 2.57 | 20.5 | 4.01 | 19.6 | 4.46 | 19.7 | 4.2 |
| 3:45 | 21.3 | 2.81 | 20.6 | 2.54 | 20.5 | 3.97 | 19.6 | 4.4 | 19.6 | 4.16 |
| 4:00 | 21.2 | 2.78 | 20.6 | 2.5 | 20.5 | 3.93 | 19.6 | 4.38 | 19.6 | 4.14 |
| 4:15 | 21.2 | 2.75 | 20.7 | 2.49 | 20.5 | 3.86 | 19.6 | 4.35 | 19.6 | 4.1 |
| 4:30 | 21.1 | 2.74 | 20.7 | 2.46 | 20.5 | 3.84 | 19.6 | 4.32 | 19.6 | 4.09 |
| 4:45 | 21.1 | 2.72 | 20.7 | 2.42 | 20.5 | 3.8 | 19.6 | 4.3 | 19.6 | 4.06 |
| 5:00 | 21.1 | 2.7 | 20.6 | 2.41 | 20.5 | 3.74 | 19.6 | 4.29 | 19.6 | 4.05 |
| Changes | 0.3 | 3.98 | 1.5 | 3.9 | 0.9 | 0.51 | 0.3 | 0.22 | 0.2 | 1.27 |
|  |  | 4.82 |  | 4.69 |  | 2.4 |  | 1.94 |  | 2.28 |

TABLE 1C

Acetic Anhydride alone: 200 microliters

| Time (Min) | Trial #1 Temp: C. | pH | Trial #2 Temp: C. | pH | Trial #3 Temp: C. | pH | Trial #4 Temp: C. | pH | Trial #5 Temp: C. | pH |
|---|---|---|---|---|---|---|---|---|---|---|
| 0:00 | 17.50 | 7.42 | 19.30 | 6.35 | 19.60 | 5.92 | 19.25 | 6.28 | 19.90 | 5.92 |
| 0:15 | 18.15 | 3.65 | 20.25 | 3.56 | 21.10 | 5.64 | 19.70 | 6.14 | 20.65 | 5.30 |
| 0:30 | 18.20 | 3.54 | 20.25 | 3.41 | 20.35 | 5.62 | 19.70 | 5.21 | 20.60 | 5.17 |
| 0:45 | 18.25 | 3.50 | 20.30 | 3.28 | 20.30 | 5.50 | 19.70 | 4.91 | 20.59 | 5.01 |
| 1:00 | 18.25 | 3.36 | 20.30 | 3.21 | 20.30 | 5.41 | 19.55 | 4.80 | 20.35 | 4.91 |
| 1:15 | 18.25 | 3.27 | 20.30 | 3.16 | 20.25 | 5.23 | 19.55 | 4.78 | 20.31 | 4.80 |
| 1:30 | 18.25 | 3.20 | 20.30 | 3.07 | 20.25 | 5.01 | 19.55 | 4.72 | 20.27 | 4.68 |
| 1:45 | 18.25 | 3.12 | 20.30 | 3.03 | 2.25 | 4.64 | 19.60 | 4.66 | 20.20 | 4.56 |
| 2:00 | 18.25 | 3.09 | 20.30 | 2.95 | 20.25 | 4.49 | 19.60 | 5.44 | 20.15 | 4.51 |
| 2:15 | 18.25 | 3.03 | 20.30 | 2.92 | 20.15 | 4.39 | 19.60 | 4.45 | 20.14 | 4.51 |
| 2:30 | 18.20 | 2.96 | 20.30 | 2.89 | 20.15 | 4.33 | 19.45 | 4.20 | 20.12 | 4.45 |
| 2:45 | 18.15 | 2.92 | 20.30 | 2.85 | 20.15 | 4.23 | 19.45 | 4.13 | 20.10 | 4.39 |
| 3:00 | 18.15 | 2.90 | 20.30 | 2.82 | 20.15 | 4.17 | 19.44 | 4.06 | 20.10 | 4.33 |
| 3:15 | 18.15 | 2.88 | 20.35 | 2.78 | 20.15 | 4.09 | 19.44 | 4.02 | 20.10 | 4.29 |
| 3:30 | 18.15 | 2.84 | 20.35 | 2.75 | 20.15 | 4.07 | 19.44 | 3.99 | 20.09 | 4.26 |
| 3:45 | 18.15 | 2.81 | 20.36 | 2.69 | 20.15 | 4.01 | 19.43 | 3.95 | 20.08 | 4.19 |
| 4:00 | 18.10 | 2.78 | 20.35 | 2.69 | 20.15 | 3.98 | 19.42 | 3.93 | 20.07 | 4.16 |
| 4:15 | 18.10 | 2.75 | 20.35 | 2.68 | 20.15 | 3.93 | 19.41 | 3.90 | 20.05 | 4.13 |
| 4:30 | 18.05 | 2.74 | 20.35 | 2.66 | 20.15 | 3.90 | 19.41 | 3.89 | 20.02 | 4.11 |
| 4:45 | 18.05 | 2.72 | 20.35 | 2.63 | 20.10 | 3.86 | 19.40 | 3.87 | 20.01 | 4.08 |
| 5:00 | 18.05 | 2.70 | 20.35 | 2.93 | 20.10 | 3.82 | 19.40 | 3.86 | 20.01 | 4.07 |
| Changes | 0.75 | 3.88 | 0.95 | 2.94 | 0.75 | 0.30 | 0.45 | 1.07 | 0.75 | 0.75 |
|  |  | 2.70 |  | 3.42 |  | 2.10 |  | 2.42 |  | 1.85 |

TABLE 1D

Acetic Anhydride alone: 300 microliters

| Time (Min) | Trial #1 Temp: C. | pH | Trial #2 Temp: C. | pH | Trial #3 Temp: C. | pH | Trial #4 Temp: C. | pH | Trial #5 Temp: C. | pH |
|---|---|---|---|---|---|---|---|---|---|---|
| 0:00 | 13.8 | 6.56 | 17 | 6.26 | 18 | 5.47 | 19 | 5.53 | 18.7 | 5.39 |
| 0:15 | 14.9 | 5.16 | 18.3 | 3.67 | 18.8 | 3.76 | 19.4 | 4.63 | 19.1 | 3.92 |
| 0:30 | 14.9 | 4.68 | 18.2 | 3.42 | 19 | 3.58 | 19.6 | 4.42 | 19.2 | 3.76 |
| 0:45 | 14.9 | 4.42 | 18.1 | 3.3 | 19.2 | 3.47 | 19.6 | 4.36 | 19.3 | 3.74 |
| 1:00 | 14.9 | 4.33 | 17.8 | 3.23 | 19.2 | 3.4 | 19.6 | 4.3 | 19.4 | 3.72 |
| 1:15 | 14.9 | 4.25 | 17.7 | 3.14 | 19.3 | 3.34 | 19.6 | 4.23 | 19.5 | 3.72 |
| 1:30 | 14.9 | 4.14 | 17.7 | 3.08 | 19.3 | 3.3 | 19.6 | 4.16 | 19.5 | 3.72 |
| 1:45 | 14.9 | 4.06 | 17.7 | 2.96 | 19.4 | 3.26 | 19.6 | 4.11 | 19.5 | 3.72 |
| 2:00 | 14.9 | 3.99 | 17.7 | 2.93 | 19.3 | 3.19 | 19.6 | 4.05 | 19.6 | 3.72 |

TABLE 1D-continued

Acetic Anhydride alone: 300 microliters

| Time (Min) | Trial #1 | | Trial #2 | | Trial #3 | | Trial #4 | | Trial #5 | |
|---|---|---|---|---|---|---|---|---|---|---|
| | Temp: C. | pH | Temp: C. | pH | Temp: C. | pH | Temp: C. | pH | Temp: C. | pH |
| 2:15 | 15 | 3.91 | 17.6 | 2.87 | 19.3 | 3.15 | 19.6 | 4 | 19.6 | 3.72 |
| 2:30 | 15 | 3.83 | 17.6 | 2.84 | 19.3 | 3.11 | 19.6 | 3.96 | 19.6 | 3.72 |
| 2:45 | 15 | 3.76 | 17.6 | 2.78 | 19.3 | 3.07 | 19.6 | 3.9 | 19.6 | 3.71 |
| 3:00 | 15 | 3.75 | 17.6 | 2.75 | 19.2 | 3 | 19.5 | 3.87 | 19.6 | 3.68 |
| 3:15 | 15 | 3.75 | 17.5 | 2.67 | 19.2 | 2.96 | 19.5 | 3.8 | 19.6 | 3.66 |
| 3:30 | 15 | 3.7 | 17.5 | 2.64 | 19.2 | 2.94 | 19.5 | 3.78 | 19.6 | 3.64 |
| 3:45 | 15 | 3.63 | 17.5 | 2.63 | 19.2 | 2.89 | 19.5 | 3.74 | 19.6 | 3.61 |
| 4:00 | 15 | 3.62 | 17.5 | 2.59 | 19.2 | 2.85 | 19.5 | 3.72 | 19.6 | 3.6 |
| 4:15 | 15 | 3.58 | 17.5 | 2.55 | 19.1 | 2.83 | 19.4 | 3.68 | 19.6 | 3.58 |
| 4:30 | 15 | 3.55 | 17.4 | 2.52 | 19.1 | 2.8 | 19.4 | 3.66 | 19.6 | 3.57 |
| 4:45 | 15 | 3.52 | 17.4 | 2.48 | 19.1 | 2.77 | 19.4 | 3.62 | 19.5 | 3.54 |
| 5:00 | 15 | 3.48 | 17.4 | 2.47 | 19 | 2.74 | 19.4 | 3.6 | 19.5 | 3.52 |
| 4:45 | 15 | 3.46 | 17.4 | 2.48 | 19.1 | 2.77 | 19.4 | 3.62 | 19.5 | 3.54 |
| 5:00 | 15 | 3.45 | 17.4 | 2.47 | 19 | 2.74 | 19.4 | 3.6 | 19.5 | 3.52 |
| Changes | 1.2 | 1.88 | 1.3 | 2.84 | 1.4 | 1.89 | 0.6 | 1.11 | 0.9 | 1.63 |
| | | 3.11 | | 3.79 | | 2.73 | | 1.93 | | 1.87 |

TABLE 1E

Acetic Anhydride alone: 500 microliters

| Time (Min) | Trial #1 | | Trial #2 | | Trial #3 | | Trial #4 | | Trial #5 | |
|---|---|---|---|---|---|---|---|---|---|---|
| | Temp: C. | pH | Temp: C. | pH | Temp: C. | pH | Temp: C. | pH | Temp: C. | pH |
| 0:00 | 19.7 | 6.57 | 19.4 | 5.6 | 19.5 | 5.7 | 19.2 | 6.32 | 20.2 | 5.5 |
| 0:15 | 20.3 | 6.45 | 20.2 | 3.78 | 20.3 | 5.6 | 19.9 | 6.25 | 21.5 | 5.4 |
| 0:30 | 20.1 | 6.3 | 20.2 | 3.62 | 20.3 | 5.61 | 19.9 | 4.4 | 21.4 | 5.27 |
| 0:45 | 20.1 | 6.2 | 20.2 | 3.45 | 20.1 | 5.46 | 19.9 | 3.9 | 21.4 | 5.11 |
| 1:00 | 20.1 | 6.22 | 20.1 | 3.36 | 20 | 5.39 | 19.6 | 3.69 | 20.9 | 5 |
| 1:15 | 20.1 | 6.21 | 20.1 | 3.34 | 19.9 | 5.2 | 19.6 | 3.68 | 20.8 | 4.84 |
| 1:30 | 19.9 | 6.11 | 20.1 | 3.24 | 19.9 | 4.96 | 19.6 | 3.61 | 20.7 | 4.75 |
| 1:45 | 19.8 | 6.11 | 20.1 | 3.21 | 19.9 | 4.82 | 19.6 | 3.6 | 20.7 | 4.61 |
| 2:00 | 19.8 | 6.04 | 20.1 | 3.13 | 19.8 | 4.67 | 19.6 | 3.6 | 20.6 | 4.54 |
| 2:15 | 19.8 | 6.02 | 20 | 3.09 | 19.8 | 4.55 | 19.6 | 3.6 | 20.6 | 4.61 |
| 2:30 | 19.8 | 5.95 | 20 | 3.06 | 19.8 | 4.45 | 19.3 | 3.6 | 20.6 | 4.54 |
| 2:45 | 19.8 | 5.89 | 20 | 3.01 | 19.8 | 4.3 | 19.3 | 3.6 | 20.5 | 4.48 |
| 3:00 | 19.8 | 5.87 | 20 | 2.98 | 19.8 | 4.21 | 19.3 | 3.55 | 20.5 | 4.4 |
| 3:15 | 19.7 | 5.82 | 20 | 2.95 | 19.8 | 4.16 | 19.3 | 3.55 | 20.5 | 4.36 |
| 3:30 | 19.7 | 5.75 | 20 | 2.92 | 19.8 | 4.13 | 19.3 | 3.52 | 20.5 | 4.32 |
| 3:45 | 19.7 | 5.67 | 20 | 2.91 | 19.8 | 4.05 | 19.3 | 3.49 | 20.4 | 4.21 |
| 4:00 | 19.7 | 5.65 | 20 | 2.88 | 19.8 | 4.03 | 19.2 | 3.47 | 20.4 | 4.18 |
| 4:15 | 19.7 | 5.55 | 20 | 2.87 | 19.8 | 3.99 | 19.2 | 3.45 | 20.4 | 4.15 |
| 4:30 | 19.6 | 5.5 | 20 | 2.85 | 19.8 | 3.95 | 19.2 | 3.45 | 20.4 | 4.13 |
| 4:45 | 19.6 | 5.41 | 20 | 2.84 | 19.7 | 3.92 | 19.2 | 3.43 | 20.4 | 4.1 |
| 5:00 | 19.6 | 5.33 | 20 | 2.84 | 19.7 | 3.9 | 19.2 | 3.42 | 20.4 | 4.08 |
| Changes | 0.6 | 0.27 | 0.8 | 1.98 | 0.8 | 0.09 | 0.7 | 1.92 | 1.3 | 0.23 |
| | | 1.24 | | 2.76 | | 1.8 | | 2.9 | | 1.42 |

Example 2

Acetyl Chloride

Acetyl Chloride was injected alone into porcine liver under identical conditions as in Example 1. A total of 23 runs were conducted using volumes of 100, 200, 300, and 500 microliters of Acetyl Chloride. The temperature change observed in these trials using Acetyl Chloride ranged from 4.3 degrees to 37.7 degrees. Although the results varied, the overall temperature changes observed using Acetyl Chloride were significantly higher than the values obtained using Acetic Anhydride. Higher volumes of Acetyl Chloride did not correlate with greater temperature changes as originally expected. From these trials, it was observed that increased volumes of Acetyl Chloride produce less measured temperature change. This observation may be due to the conduit phenomenon. Perhaps with the increased volume of Acetyl Chloride, the solution is capable of burning into vessels within the liver parenchyma and tracking away from the temperature probe rather than staying in proximity to the probe for accurate measurement.

Additionally, trials using a plastic dilator were conducted to determine the effectiveness of the plastic dilator as a delivery tool for the Acetyl Chloride. Similar temperature changes were recorded using this delivery tool and no complications arose during injection sequences using the plastic dilator. After three runs using the plastic dilator, the Acetyl Chloride had destroyed the lumen of the dilator making subsequent injections impossible.

The results of all tests are reported below in Tables 2A-2F.

Based on visual destruction patterns produced by Acetic Anhydride, larger volumes generally yielded larger areas of tissue destruction although large volumes had a tendency to regurgitate superficially through the injection site or destroy tissue at a more distant site through the conduit phenomenon. In general, Acetyl Chloride produced more violent and rapid tissue destruction than Acetic Anhydride.

TABLE 2A

Acetyl Chloride Alone: 100 microliters - different temp probe

| Time (Min) | Trial #1 Temp: C. | Trial #2 Temp: C. | Trial #3 Temp: C. | Trial #4 Temp: C. | Trial #5 Temp: C. |
|---|---|---|---|---|---|
| 0:00 | 16.4 | 17.1 | 17.4 | 16.6 | 17 |
| 0:15 | 20.3 | 52.5 | 52.8 | 51.1 | 54.7 |
| 0:30 | 22.5 | 32 | 39 | 42.2 | 32.3 |
| 0:45 | 21.5 | 27.5 | 33.5 | 33.9 | 27.3 |
| 1:00 | 21 | 25 | 30.6 | 30.7 | 25.7 |
| 1:15 | 20.2 | 24 | 28.4 | 27.8 | 23.9 |
| 1:30 | 19.6 | 23.5 | 27 | 26.2 | 23.1 |
| 1:45 | 19 | 22.7 | 25.6 | 25 | 22.3 |

TABLE 2A-continued

Acetyl Chloride Alone: 100 microliters - different temp probe

| Time (Min) | Trial #1 Temp: C. | Trial #2 Temp: C. | Trial #3 Temp: C. | Trial #4 Temp: C. | Trial #5 Temp: C. |
|---|---|---|---|---|---|
| 2:00 | 18.4 | 22.1 | 24.7 | 24.2 | 21.6 |
| 2:15 | 18.3 | 21.4 | 23.9 | 23.2 | 21.1 |
| 2:30 | 18.1 | 21.1 | 23.3 | 22.6 | 20.6 |
| 2:45 | 18 | 20.6 | 22.6 | 22 | 20.2 |
| 3:00 | 17.9 | 20.3 | 22.1 | 21.5 | 19.9 |
| 3:15 | 17.8 | 20.1 | 21.7 | 21.1 | 19.6 |
| 3:30 | 17.7 | 19.8 | 213 | 20.7 | 19.3 |
| 3:45 | 17.6 | 19.5 | 21 | 20.4 | 19.1 |
| 4:00 | 17.5 | 19.4 | 20.7 | 20.1 | 18.9 |
| 4:15 | 17.5 | 19.2 | 20.4 | 19.9 | 18.9 |
| 4:30 | 17.4 | 19 | 20.2 | 19.6 | 18.6 |
| 4:45 | 17.3 | 18.8 | 20 | 19.4 | 18.4 |
| 5:00 | 17.3 | 18.6 | 19.8 | 19.2 | 18.3 |
| Changes | 6.1 | 35.4 | 35.4 | 34.5 | 37.7 |

TABLE 2B

Acetyl Chloride alone: 100 microliters

| | Trial #1 | | Trial #2 | | Trial #3 | | Trial #4 | |
|---|---|---|---|---|---|---|---|---|
| Time (Min) | Temp: C. | pH | Temp: C. | pH | Temp: C. | pH | Temp: C. | pH |
| 0:00 | 20.5 | 6.14 | 19.7 | 6.55 | 18.8 | 6.5 | 17.4 | 5.7 |
| 0:15 | 34.2 | 3.1 | 30.2 | 4.67 | 26.3 | 4.62 | 23.6 | 4.82 |
| 0:30 | 30.1 | 2.5 | 27.4 | 3.59 | 24 | 3.32 | 23.2 | 4.57 |
| 0:45 | 28.5 | 2.25 | 25.1 | 2.35 | 23.7 | 3.22 | 23 | 4.51 |
| 1:00 | 27.4 | 2.02 | 24.5 | 2.27 | 23.4 | 2.12 | 22.8 | 4.48 |
| 1:15 | 26.2 | 1.8 | 23.6 | 1.97 | 23.1 | 2.04 | 22.2 | 4.41 |
| 1:30 | 25.2 | 1.67 | 22.2 | 1.85 | 22.7 | 1.99 | 21.7 | 4.34 |
| 1:45 | 25.1 | 1.53 | 22.2 | 1.79 | 22.6 | 1.93 | 21.5 | 4.31 |
| 2:00 | 24.5 | 1.47 | 21.9 | 1.7 | 22.2 | 1.9 | 21.3 | 4.27 |
| 2:15 | 24 | 1.38 | 21.6 | 1.62 | 22 | 1.84 | 21.1 | 4.24 |
| 2:30 | 23.6 | 1.29 | 21.5 | 1.52 | 21.7 | 1.81 | 20.9 | 4.2 |
| 2:45 | 23.3 | 1.19 | 21.5 | 1.46 | 21.5 | 1.77 | 20.8 | 4.18 |
| 3:00 | 22.9 | 1.1 | 21.5 | 1.42 | 21.3 | 1.74 | 20.8 | 4.16 |
| 3:15 | 22.6 | 1.05 | 21.4 | 1.4 | 21.2 | 1.71 | 20.7 | 4.14 |
| 3:30 | 22.4 | 1 | 21.2 | 1.34 | 21.1 | 1.69 | 20.6 | 4.12 |
| 3:45 | 22.2 | 0.95 | 21.1 | 1.29 | 21 | 1.66 | 20.6 | 4.09 |
| 4:00 | 22 | 0.92 | 20.9 | 1.24 | 20.9 | 1.64 | 20.5 | 4.06 |
| 4:15 | 21.8 | 0.84 | 20.9 | 1.21 | 20.8 | 1.61 | 20.4 | 4.04 |
| 4:30 | 21.6 | 0.8 | 20.8 | 1.17 | 20.7 | 1.6 | 2.3 | 4.03 |
| 4:45 | 21.5 | 0.75 | 20.7 | 1.12 | 20.6 | 1.55 | 20.3 | 4.02 |
| 5:00 | 21.4 | 0.72 | 20.7 | 1.1 | 20.5 | 1.54 | 20.3 | 4 |
| Changes | 13.7 | 3.64 | 10.5 | 2.96 | 7.5 | 3.18 | 6.2 | 1.13 |
| | | 5.42 | | 5.45 | | 4.96 | | 1.7 |

TABLE 2C

Acetyl Chloride alone: 200 microliters

| | Trial #1 | | Trial #2 | | Trial #3 | | Trial #4 | |
|---|---|---|---|---|---|---|---|---|
| Time (Min) | Temp: C. | pH | Temp: C. | pH | Temp: C. | pH | Temp: C. | pH |
| 0:00 | 21.2 | 7.22 | 20 | 6.52 | 18.9 | 6.33 | 18.4 | 6.05 |
| 0:15 | 38.4 | 4.58 | 26.1 | 4.96 | 30.1 | 5.33 | 25.3 | 2.9 |
| 0:30 | 37 | 4.47 | 26.9 | 4.47 | 29 | 4.9 | 26.6 | 2.61 |
| 0:45 | 35.1 | 4.23 | 27.2 | 4.52 | 28.7 | 4.81 | 26.4 | 2.54 |
| 1:00 | 33.3 | 4.04 | 26.5 | 4.22 | 27.5 | 4.45 | 25.6 | 2.47 |
| 1:15 | 31.3 | 3.85 | 25.9 | 3.67 | 26.5 | 4.22 | 25.1 | 2.43 |
| 1:30 | 30.3 | 3.69 | 25.7 | 3.36 | 25.4 | 4.03 | 24.7 | 2.41 |
| 1:45 | 29 | 3.54 | 25 | 3.15 | 24.8 | 3.84 | 24.1 | 2.34 |
| 2:00 | 28.2 | 3.45 | 24.4 | 3.1 | 24.1 | 3.78 | 23.8 | 2.3 |
| 2:15 | 27.4 | 3.28 | 24.1 | 2.99 | 23.6 | 3.6 | 23.5 | 2.26 |
| 2:30 | 26.7 | 3.14 | 23.5 | 2.87 | 23.2 | 3.47 | 23.2 | 2.21 |
| 2:45 | 26.3 | 3.05 | 23.2 | 2.82 | 22.7 | 3.39 | 22.8 | 2.14 |
| 3:00 | 26 | 2.92 | 23..1 | 2.74 | 22.5 | 3.34 | 22.6 | 2.12 |

TABLE 2C-continued

Acetyl Chloride alone: 200 microliters

| Time (Min) | Trial #1 Temp: C. | pH | Trial #2 Temp: C. | pH | Trial #3 Temp: C. | pH | Trial #4 Temp: C. | pH |
|---|---|---|---|---|---|---|---|---|
| 3:15 | 25.4 | 2.84 | 22.7 | 2.61 | 22.1 | 3.25 | 22.4 | 2.07 |
| 3:30 | 25 | 2.74 | 22.5 | 2.54 | 21.9 | 3.19 | 22 | 2.03 |
| 3:45 | 24.6 | 2.68 | 22.3 | 2.46 | 21.6 | 3.12 | 21.9 | 1.99 |
| 4:00 | 24.4 | 2.59 | 22.1 | 2.44 | 21.5 | 3.05 | 21.7 | 1.96 |
| 4:15 | 24 | 2.53 | 21.9 | 2.39 | 21.3 | 3.02 | 21.6 | 1.92 |
| 4:30 | 23.9 | 2.47 | 21.8 | 2.33 | 21.2 | 2.99 | 21.4 | 1.89 |
| 4:45 | 23.9 | 2.39 | 21.7 | 2.29 | 21 | 2.92 | 21.1 | 1.85 |
| 5:00 | 23.5 | 2.33 | 21.5 | 2.25 | 20.9 | 2.88 | 21 | 1.83 |
| Changes | 17.2 | 2.75 | 7.2 | 2.05 | 11.2 | 1.43 | 8.2 | 3.44 |
|  |  | 4.89 |  | 4.27 |  | 3.45 |  | 4.22 |

TABLE 2D

Acetyl Chloride alone: 300 microliters

| Time (Min) | Trial #1 Temp: C. | pH | Trial #2 Temp: C. | pH | Trial #3 Temp: C. | pH | Trial #4 Temp: C. | pH |
|---|---|---|---|---|---|---|---|---|
| 0:00 | 19.1 | 7.39 | 19.8 | 6.38 | 19.1 | 6.55 | 18.1 | 6.94 |
| 0:15 | 23.4 | 3.25 | 29.3 | 3.72 | 26.5 | 3.8 | 21.4 | 5.94 |
| 0:30 | 23.1 | 3.12 | 27.5 | 3.45 | 25.5 | 2.44 | 22.4 | 5.57 |
| 0:45 | 22.8 | 3.1 | 26.6 | 3.24 | 25.2 | 2.28 | 23.2 | 2.89 |
| 1:00 | 22.6 | 3.09 | 26.5 | 3.12 | 24.9 | 2.13 | 23.6 | 2.81 |
| 1:15 | 22.5 | 3.08 | 25.7 | 3.06 | 24.5 | 2.04 | 24.2 | 2.81 |
| 1:30 | 22.5 | 3.05 | 25.4 | 3.03 | 24.4 | 2.02 | 24.4 | 2.75 |
| 1:45 | 22.3 | 3.04 | 24.8 | 2.93 | 24.1 | 2 | 24.4 | 2.75 |
| 2:00 | 22.3 | 3.03 | 24.5 | 2.89 | 23.9 | 1.97 | 24.4 | 2.71 |
| 2:15 | 22.2 | 2.93 | 24.3 | 2.84 | 23.8 | 1.94 | 24.3 | 2.68 |
| 2:30 | 22.2 | 2.81 | 24 | 2.88 | 23.5 | 1.92 | 24.1 | 2.61 |
| 2:45 | 22.2 | 2.67 | 23.8 | 2.76 | 23.3 | 1.89 | 23.9 | 2.61 |
| 3:00 | 22.1 | 2.51 | 23.5 | 2.73 | 23.3 | 1.87 | 23.7 | 2.56 |
| 3:15 | 22.1 | 2.46 | 23.1 | 2.66 | 23.1 | 1.86 | 23.6 | 2.52 |
| 3:30 | 22 | 2.38 | 23.1 | 2.62 | 22.8 | 1.84 | 23.3 | 2.48 |
| 3:45 | 22 | 2.3 | 22.8 | 2.56 | 22.6 | 1.81 | 23.1 | 2.43 |
| 4:00 | 22 | 2.22 | 22.6 | 2.52 | 22.4 | 1.79 | 23 | 2.4 |
| 4:15 | 22 | 217 | 22.5 | 2.48 | 22.3 | 1.78 | 22.7 | 2.36 |
| 4:30 | 21.97 | 2.13 | 22.2 | 2.44 | 22.2 | 1.76 | 22.6 | 2.31 |
| 4:45 | 21.8 | 20.7 | 22.1 | 2.41 | 22 | 1.77 | 22.5 | 2.29 |
| 5:00 | 21.76 | 2.02 | 22 | 2.38 | 22.1 | 1.75 | 22.4 | 2.26 |
| Changes | 4.3 | 4.27 | 9.5 | 2.93 | 7.4 | 4.11 | 6.3 | 1.37 |
|  |  | 5.37 |  | 4 |  | 4.8 |  | 4.68 |

TABLE 2E

Acetyl Chloride alone: 500 microliters

| Time (Min) | Trial #1 Temp: C. | pH | Trial #2 Temp: C. | pH | Trial #3 Temp: C. | pH |
|---|---|---|---|---|---|---|
| 0:00 | 19.4 | 7.55 | 17.7 | 7.5 | 16.6 | 7.5 |
| 0:15 | 45.5 | 4.25 | 29.5 | 4.6 | 29.4 | 3.77 |
| 0:30 | 43.1 | 4.05 | 29.1 | 4.36 | 28.4 | 3.66 |
| 0:45 | 40 | 3.98 | 29 | 4 | 27.7 | 3.56 |
| 1:00 | 36.1 | 3.71 | 28.2 | 3.81 | 26.3 | 3.41 |
| 1:15 | 32.1 | 3.36 | 27.4 | 3.59 | 25.2 | 3.35 |
| 1:30 | 30.3 | 3.23 | 26.5 | 3.51 | 24.8 | 3.31 |
| 1:45 | 28.8 | 3.11 | 25.7 | 3.42 | 24 | 3.27 |
| 2:00 | 27.5 | 2.99 | 25.3 | 3.33 | 23.5 | 3.23 |
| 2:15 | 26.3 | 2.89 | 24.7 | 3.25 | 22.6 | 3.2 |
| 2:30 | 25.5 | 2.82 | 24.2 | 3.21 | 22.8 | 3.17 |
| 2:45 | 24.9 | 2.75 | 23.8 | 3.17 | 22.1 | 3.15 |

TABLE 2E-continued

Acetyl Chloride alone: 500 microliters

| Time (Min) | Trial #1 Temp: C. | pH | Trial #2 Temp: C. | pH | Trial #3 Temp: C. | pH |
|---|---|---|---|---|---|---|
| 3:00 | 24.3 | 2.7 | 23.4 | 3.14 | 21.8 | 3.13 |
| 3:15 | 23.6 | 2.68 | 23 | 3.05 | 21.4 | 3.11 |
| 3:30 | 23.1 | 2.64 | 22.6 | 3.01 | 21.2 | 3.08 |
| 3:45 | 22.8 | 2.61 | 22.3 | 2.96 | 20.8 | 3.02 |
| 4:00 | 22.5 | 2.59 | 22 | 2.92 | 20.3 | 3.02 |
| 4:15 | 22.2 | 2.58 | 21.8 | 2.87 | 20.1 | 3.01 |
| 4:30 | 21.8 | 2.56 | 21.7 | 2.84 | 20 | 3.01 |
| 4:45 | 21.7 | 2.55 | 21.5 | 2.8 | 19.9 | 2.99 |
| 5:00 | 21.5 | 2.54 | 21.3 | 2.78 | 19.8 | 2.97 |
| Changes | 26.1 | 3.5 | 11.8 | 3.14 | 12.8 | 3.84 |
|  |  | 5.01 |  | 4.72 |  | 4.53 |

TABLE 2F

Acetyl Chloride - plastic dilator trial

| Time (Min) | Trial #1 Temp: C. | pH | Trial #2 Temp: C. | pH | Trial #3 Temp: C. | pH | Trial #4 Temp: C. |
|---|---|---|---|---|---|---|---|
| 0:00 | 20.9 | 7 | 20.1 | 6.21 | 19.2 | 6.2 | Ruined |
| 0:15 | 30.8 | 1.54 | 28.4 | 5.55 | 27.5 | 3.31 | |
| 0:30 | 28.5 | 1.14 | 22.5 | 4.57 | 26.9 | 3.11 | |
| 0:45 | 27.1 | 0.92 | 22.4 | 4.52 | 26..1 | 2.8 | |
| 1:00 | 25.3 | 0.56 | 22.1 | 4.46 | 25.4 | 2.52 | |
| 1:15 | 25.1 | 0.45 | 22.5 | 4.2 | 24.9 | 2.23 | |
| 1:30 | 24.6 | 0.46 | 22.4 | 4 | 24.2 | 1.97 | |
| 1:45 | 24.2 | 0.41 | 22.3 | 3.81 | 23.7 | 1.57 | |
| 2:00 | 23.9 | 0.37 | 22.3 | 3.68 | 23.1 | 1.2 | |
| 2:15 | 23.5 | 0.33 | 22.2 | 3.56 | 22.7 | 1.14 | |
| 2:30 | 23.3 | 0.3 | 22 | 3.45 | 22.2 | 0.9 | |
| 2:45 | 23 | 0.29 | 21.9 | 3.39 | 21.8 | 0.89 | |
| 3:00 | 22.8 | 0.26 | 21.8 | 3.32 | 21.3 | 0.76 | |
| 3:15 | 22.5 | 0.25 | 21.7 | 3.27 | 21.1 | 0.72 | |
| 3:30 | 22.3 | 0.24 | 21.6 | 3.19 | 20.9 | 0.69 | |
| 3:45 | 22.1 | 0.21 | 21.6 | 3.15 | 20.7 | 0.66 | |
| 4:00 | 21.8 | 0.2 | 21.5 | 3.13 | 20.6 | 0.63 | |
| 4:15 | 21.7 | 0.18 | 21.4 | 3.06 | 20.4 | 0.6 | |
| 4:30 | 21.6 | 0.17 | 21.3 | 3.01 | 20.2 | 0.58 | |
| 4:45 | 21.4 | 0.17 | 21.2 | 2.96 | 21.8 | 0.57 | |
| 5:00 | 21.2 | 0.16 | 21.1 | 2.93 | 21.7 | 0.57 | |
| Changes | 9.9 | 5.86 | 8.3 | 1.64 | 8.3 | 3.09 | NA |
| | | 6.84 | | 3.28 | | 5.63 | |

Example 3

Acetic Anhydride & Sodium Hydroxide

Solutions of Acetic Anhydride (100, 200, and 300 microliters) were reacted with 1M, 5M, 10M, and 15M NaOH. A total of 13 trials were conducted. During these trials, 100 microliters of NaOH was injected around the thermocouple probe in tissue and pH was measured to ensure proper administration. Thereafter, Acetic Anhydride was injected at the appropriate volume, and the subsequent temperature change and pH were measured. The recorded temperature change ranged from 1.4-9.4 degrees C. Although the overall energy yield from Acetic Anhydride in combination with NaOH appears to be significantly higher than Acetic Anhydride alone, it appears that a significant portion of NaOH was unable to react with the Acetic Anhydride. At the conclusion of nearly every injection sequence, the final thermocouple pH was overwhelmingly basic after five minutes. This observation may indicate poor mixing and potentially less than maximal temperature yields from these compounds. Improving mixing methods may yield larger temperature changes and increased tissue destruction capacity. The results are shown below on Tables 3A-3C.

TABLE 3A

AA 100 micro + 100 micro NaOH

| Time (Min) | 1M Trial #1 Temp: C. | pH | 1M Trial #2 Temp | pH | 5M Trial #3 Temp: C. | pH | 10M Trial #4 Temp: C. | pH | 15M Trial #5 Temp: C. | pH |
|---|---|---|---|---|---|---|---|---|---|---|
| Pre-base | 14.4 | 7.49 | 14.7 | 7.23 | 16.6 | 7.76 | 18 | 7.96 | 19.2 | 7.99 |
| 0:00 | 17.7 | 13.76 | 15.9 | 14.64 | 16.7 | 15.5 | 19.1 | 14.9 | 20.2 | 14.85 |
| 0:15 | 18.4 | 13.72 | 17.5 | 14.64 | 18.7 | 15.5 | 22.2 | 14.9 | 20.2 | 14.95 |
| 0:30 | 17.9 | 13.63 | 13.3 | 14.55 | 18.2 | 15.5 | 21.3 | 14.9 | 20.6 | 14.95 |
| 0:45 | 17.8 | 13.58 | 17.2 | 14.48 | 18 | 15.5 | 20.8 | 14.9 | 20.5 | 14.93 |
| 1:00 | 17.8 | 13.53 | 17.1 | 14.36 | 17.6 | 15.5 | 20.5 | 14.9 | 20.5 | 14.89 |
| 1:15 | 17.7 | 13.47 | 17 | 14.37 | 17.5 | 15.5 | 20.3 | 14.9 | 20.4 | 14.89 |
| 1:30 | 17.6 | 13.45 | 17 | 14.32 | 17.5 | 15.5 | 20.2 | 14.8 | 20.4 | 14.87 |
| 1:45 | 17.6 | 13.39 | 17 | 14.27 | 17.4 | 15.5 | 20 | 14.8 | 20.3 | 14.86 |
| 2:00 | 17.6 | 13.37 | 16.9 | 14.16 | 17.3 | 15.5 | 19.9 | 14.8 | 20.3 | 14.83 |
| 2:15 | 17.6 | 13.34 | 16.9 | 14.16 | 17.2 | 15.5 | 19.8 | 14.8 | 20.3 | 14.8 |
| 2:30 | 17.5 | 13.3 | 16.8 | 14.1 | 17.1 | 15.4 | 19.8 | 14.8 | 20.3 | 14.72 |
| 2:45 | 17.5 | 13.26 | 16.8 | 14.02 | 17.1 | 15.4 | 19.6 | 14.8 | 20.2 | 14.71 |
| 3:00 | 17.5 | 13.22 | 16.8 | 14.04 | 17.1 | 15.4 | 19.6 | 14.8 | 20.2 | 14.67 |
| 3:15 | 17.5 | 13.2 | 16.8 | 13.99 | 17 | 15.4 | 19.4 | 14.8 | 20.2 | 14.65 |
| 3:30 | 17.5 | 13.15 | 16.8 | 13.95 | 17 | 15.4 | 19.3 | 14.7 | 20.2 | 14.56 |
| 3:45 | 17.4 | 13.1 | 16.7 | 13.9 | 17 | 15.4 | 19.2 | 14.7 | 20.1 | 14.57 |
| 4:00 | 17.4 | 13.1 | 16.7 | 13.85 | 16.9 | 15.4 | 19.2 | 14.7 | 20.1 | 14.55 |
| 4:15 | 17.4 | 13.1 | 16.7 | 13.82 | 16.9 | 15.4 | 19.1 | 14.7 | 20.1 | 14.51 |
| 4:30 | 17.4 | 13.06 | 16.6 | 13.77 | 16.8 | 15.3 | 19 | 14.7 | 20.1 | 14.5 |
| 4:45 | 17.4 | 13.05 | 16.6 | 13.75 | 16.8 | 15.3 | 19 | 14.7 | 20.1 | 14.48 |
| 5:00 | 17.4 | 13.04 | 16.6 | 13.7 | 16.8 | 15.3 | 18.9 | 14.7 | 19.9 | 14.47 |
| Changes | 4 | −6.27 | 2.8 | −7.41 | 2.1 | −7.74 | 4.2 | −6.94 | 1.4 | −6.86 |

TABLE 3B

AA 200 micro + 100 micro NaOH

| | 1M Trial #1 | | 5M Trial #2 | | 10M Trial #3 | | 15M Trial #4 | |
|---|---|---|---|---|---|---|---|---|
| Time (Min) | Temp: C. | pH | Temp: C. | pH | Temp: C. | pH | Temp: C. | pH |
| Pre-base | 15.8 | 7.99 | 18.9 | 7.99 | 18.2 | 8.5 | 16.8 | 7.45 |
| 0:00 | 18.9 | 15.76 | 20.5 | 14.76 | 21.4 | 15.5 | 22.4 | 14.9 |
| 0:15 | 17.8 | 15.7 | 21.5 | 14.68 | 24.4 | 15.5 | 23.6 | 14.81 |
| 0:30 | 17.5 | 15.76 | 21.5 | 14.66 | 24.4 | 15.47 | 24.4 | 14.7 |
| 0:45 | 17.4 | 15.78 | 21.3 | 14.66 | 24.4 | 15.51 | 25 | 14.59 |
| 1:00 | 17.2 | 15.78 | 21.1 | 1.65 | 24 | 15.55 | 26.2 | 14.68 |
| 1:15 | 17.1 | 15.78 | 21 | 14.65 | 23.3 | 15.55 | 25 | 14.84 |
| 1:30 | 17 | 15.77 | 21 | 14.65 | 22.8 | 15.57 | 24.3 | 14.95 |
| 1:45 | 17 | 15.77 | 20.8 | 14.62 | 22.4 | 15.56 | 23.3 | 15.09 |
| 2:00 | 16.9 | 15.75 | 20.6 | 14.62 | 22.2 | 15.52 | 22.8 | 15.2 |
| 2:15 | 16.9 | 15.75 | 20.6 | 14.61 | 22.1 | 15.52 | 22 | 15.27 |
| 2:30 | 16.9 | 15.73 | 20.5 | 14.6 | 21.9 | 15.53 | 21.6 | 15.33 |
| 2:45 | 16.8 | 15.72 | 20.4 | 14.58 | 21.7 | 15.53 | 21.4 | 15.4 |
| 3:00 | 16.8 | 15.72 | 20.4 | 14.56 | 21.6 | 15.52 | 21.1 | 15.43 |
| 3:15 | 16.8 | 15.69 | 20.3 | 14.55 | 21.3 | 15.52 | 20.9 | 15.47 |
| 3:30 | 16.7 | 15.68 | 20.3 | 14.51 | 21.2 | 15.52 | 20.9 | 15.5 |
| 3:45 | 16.7 | 15.66 | 20.2 | 14.5 | 21.2 | 15.49 | 20.8 | 15.52 |
| 4:00 | 16.6 | 15.65 | 20.1 | 14.48 | 21.1 | 15.46 | 20.6 | 15.54 |
| 4:15 | 16.6 | 15.64 | 20.1 | 14.47 | 21 | 15.44 | 20.5 | 15.57 |
| 4:30 | 16.6 | 15.64 | 20 | 14.45 | 20.9 | 15.41 | 20.4 | 15.6 |
| 4:45 | 16.6 | 15.63 | 20 | 14.44 | 20.8 | 15.4 | 20.3 | 15.62 |
| 5:00 | 16.6 | 15.6 | 19.9 | 14.42 | 20.7 | 15.36 | 20.3 | 15.64 |
| Changes | 3.1 | −7.77 | 2.6 | −6.77 | 3.2 | −7 | 9.4 | −7.45 |

TABLE 3C

AA 300 micro + 100 micro NaOH

| | 1M Trial #1 | | 5M Trial #2 | | 10M Trial #3 | | 15M Trial #4 | |
|---|---|---|---|---|---|---|---|---|
| Time (Min) | Temp: C. | pH | Temp: C. | pH | Temp: C. | pH | Temp: C. | pH |
| Pre-base | 14.9 | 7.25 | 18.4 | 7.98 | 18.9 | 7.55 | 17.9 | 8 |
| 0:00 | 18.9 | 15.02 | 21.4 | 14.63 | 19.8 | 15.7 | 20.1 | 15.9 |
| 0:15 | 17.8 | 14.64 | 23.9 | 14.4 | 24.4 | 15.6 | 21.2 | 14.8 |
| 0:30 | 17.4 | 14.7 | 22.9 | 14 | 26.3 | 15.37 | 23.4 | 14.74 |
| 0:45 | 17.2 | 14.75 | 22.5 | 13.81 | 25.2 | 15.41 | 21.8 | 14.76 |
| 1:00 | 16.9 | 14 | 21.9 | 13.52 | 24.5 | 15.45 | 21.5 | 14.81 |
| 1:15 | 16.9 | 76 | 21.6 | 13.34 | 23.8 | 15.49 | 21.2 | 14.92 |
| 1:30 | 16.8 | 14.8 | 21.4 | 12.95 | 23.5 | 15.49 | 21.1 | 14.95 |
| 1:45 | 16.8 | 14.87 | 21.2 | 12.79 | 23.1 | 15.48 | 21.1 | 14.98 |
| 2:00 | 16.7 | 14.89 | 21.1 | 12.56 | 22.9 | 15.43 | 21 | 15.02 |
| 2:15 | 16.6 | 14.92 | 20.9 | 12.3 | 22.7 | 15.41 | 20.9 | 15.09 |
| 2:30 | 16.6 | 14.94 | 20.9 | 12.19 | 22.3 | 15.36 | 20.7 | 15.13 |
| 2:45 | 16.6 | 14.95 | 20.7 | 11.91 | 22.2 | 15.34 | 20.7 | 15.14 |
| 3:00 | 16.5 | 14.65 | 20.7 | 11.74 | 22.1 | 15.3 | 20.6 | 15.17 |
| 3:15 | 16.5 | 14.93 | 20.7 | 11.5 | 21.9 | 15.29 | 20.5 | 15.17 |
| 3:30 | 16.5 | 14.92 | 20.7 | 11.32 | 21.7 | 15.25 | 20.3 | 15.18 |
| 3:45 | 16.4 | 14.91 | 20.6 | 11.22 | 21.5 | 15.24 | 20.3 | 15.1 |
| 4:00 | 16.4 | 14.9 | 20.6 | 11.08 | 21.3 | 15.22 | 20.2 | 15.17 |
| 4:15 | 16.4 | 14.87 | 20.6 | 10.92 | 21.1 | 15.21 | 20.2 | 15.16 |
| 4:30 | 16.4 | 14.84 | 20.5 | 10.81 | 21 | 15.21 | 20.12 | 15.16 |
| 4:45 | 16.4 | 14.8 | 20.4 | 10.55 | 20.9 | 15.2 | 19.9 | 15.5 |
| 5:00 | 16.4 | 14.79 | 20.4 | 10.54 | 20.7 | 15.19 | 19.9 | 15.5 |
| Changes | 4 | −7.77 | 5.5 | −6.65 | 7.4 | −8.15 | 5.5 | −7.9 |

Example 4

Acetyl Chloride & Sodium Hydroxide

Solutions of Acetyl Chloride (100, 200, and 300 microliters) were reacted with 1M, 5M, 10M, and 15M NaOH. A total of 21 injections were conducted. During these trials, NaOH (either 100 or 200 microliters) was injected around the thermocouple probe as described in Example 3, and then followed with a subsequent injection of Acetyl Chloride. The temperature change observed during the reaction of NaOH with Acetyl Chloride was much greater than that observed using Acetic Anhydride. Temperature changes ranged from 7.9-32 degrees Celsius. Eleven of the twenty-one runs elicited temperature changes between 20-30 degrees Celsius in the first thirty seconds after injection. As expected, the largest temperature changes occurred with larger volumes (300 microliters) of Acetyl Chloride and NaOH. Unlike the trials using Acetic Anhydride, the final thermocouple probe pH after five minutes consistently displayed a more acidic pH when using Acetyl Chloride. This may indicate improved mixing of the acid and base solutions or it may simply indicate that Acetyl Chloride is a stronger electrophile with a greater capacity to neutralize the volume of NaOH placed into the liver parenchyma. Lastly, although the addition of NaOH did not appear to increase the maximum temperature recorded over Acetyl Chloride injected alone, it did appear to increase the rate of average temperature change observed during these runs. The test results are shown below on Tables 4A-4F.

TABLE 4A

AC 100 micro + 100 micro NaOH

| Time (Min) | 1M Trial #1 | | 5M Trial #2 | | 10M Trial #3 | | 15M Trial #4 | |
|---|---|---|---|---|---|---|---|---|
| | Temp: C. | pH | Temp: C. | pH | Temp: C. | pH | Temp: C. | pH |
| Pre-base | 19 | 9.66 | 17.3 | 7.93 | 18.3 | 7.91 | 20.6 | 7.43 |
| 0:00 | 19.7 | 14.35 | 17.4 | 15.01 | 18.5 | 15.45 | 21 | 15.25 |
| 0:15 | 28.3 | 13.35 | 34.3 | 14.73 | 48.1 | 12.43 | 28.8 | 12.72 |
| 0:30 | 25 | 11.23 | 26.9 | 15.45 | 43.3 | 12.77 | 26.6 | 12.67 |
| 0:45 | 23.6 | 11.99 | 22.1 | 15.89 | 32.6 | 12.96 | 24.6 | 12.56 |
| 1:00 | 22.6 | 11.96 | 21.4 | 15.99 | 28.6 | 13.01 | 23.4 | 12.48 |
| 1:15 | 21.8 | 11.94 | 20.5 | 15.99 | 27.6 | 13.03 | 22.4 | 12.25 |
| 1:30 | 21.2 | 11.65 | 20.5 | 15.99 | 26.2 | 13.01 | 21.8 | 12.15 |
| 1:45 | 20.9 | 12.29 | 19.7 | 15.99 | 24.4 | 12.99 | 21.5 | 11.95 |
| 2:00 | 20.6 | 12.33 | 19.4 | 15.99 | 23.2 | 12.98 | 21.2 | 11.86 |
| 2:15 | 20.4 | 12.35 | 19.1 | 15.99 | 22.8 | 12.97 | 21 | 11.75 |
| 2:30 | 20.1 | 12.27 | 18.9 | 15.99 | 22.1 | 12.94 | 20.7 | 11.66 |
| 2:45 | 20.1 | 12.26 | 18.7 | 15.99 | 21.7 | 12.94 | 20.6 | 11.55 |
| 3:00 | 20 | 12.24 | 18.6 | 15.99 | 21.5 | 12.92 | 20.5 | 11.49 |
| 3:15 | 19.9 | 12.35 | 18.4 | 15.99 | 21.2 | 12.9 | 20.3 | 11.38 |
| 3:30 | 19.6 | 12.33 | 18.3 | 15.99 | 20.8 | 12.9 | 20.3 | 11.34 |
| 3:45 | 19.6 | 12.12 | 18.2 | 15.99 | 20.6 | 12.9 | 20.1 | 11.28 |
| 4:00 | 16.5 | 12.4 | 18.1 | 15.99 | 20.4 | 12.9 | 20 | 11.23 |
| 4:15 | 19.4 | 12.44 | 18 | 15.99 | 20.2 | 12.9 | 20 | 11.16 |
| 4:30 | 19.3 | 12.43 | 17.9 | 15.99 | 20 | 12.89 | 19.9 | 11.12 |
| 4:45 | 19.2 | 12.39 | 17.8 | 15.99 | 20 | 12.87 | 19.9 | 11.07 |
| 5:00 | 19.1 | 12.37 | 17.7 | 15.99 | 20 | 12.86 | 19.8 | 11.02 |
| Changes | 9.3 | −4.69 | 17 | −7.08 | 29.8 | −7.54 | 8.2 | −7.82 |

TABLE 4B

AC 200 micro + 100 micro NaOH

| Time (Min) | 1M Trial #1 | | 5M Trial #2 | | 10M Trial #3 | | 15M Trial #4 | |
|---|---|---|---|---|---|---|---|---|
| | Temp: C. | pH | Temp: C. | pH | Temp: C. | pH | Temp: C. | pH |
| Pre-base | 18 | 7.56 | 16.8 | 8.1 | 16.6 | 7.63 | 16.8 | 7.7 |
| 0:00 | 28 | 13.32 | 24.7 | 15.56 | 18.3 | 15.5 | 18.2 | 15.5 |
| 0:15 | 33.4 | 12.54 | 21.8 | 14.5 | 48.8 | 12.07 | 40.1 | 7.45 |
| 0:30 | 32 | 6.22 | 21.4 | 14.7 | 42.5 | 13.1 | 37.5 | 5 |
| 0:45 | 27.6 | 5.33 | 21.6 | 15 | 37.7 | 13.8 | 32.3 | 4.34 |
| 1:00 | 25.2 | 3.95 | 21.6 | 15.54 | 33.8 | 14.3 | 29.2 | 4.18 |
| 1:15 | 24.7 | 3.09 | 21.5 | 15.59 | 29.4 | 14.67 | 26.7 | 4.57 |
| 1:30 | 23.6 | 3.07 | 21.3 | 15.63 | 27.5 | 14.93 | 25 | 5.07 |
| 1:45 | 22.5 | 2.85 | 20.9 | 15.7 | 26.3 | 15.02 | 24.4 | 5.56 |
| 2:00 | 22.2 | 2.75 | 20.6 | 15.74 | 25 | 15.23 | 22.7 | 5.96 |
| 2:15 | 21.8 | 2.67 | 20.4 | 15.78 | 23.7 | 15.38 | 21.7 | 6.02 |
| 2:30 | 21.5 | 2.63 | 20.2 | 15.8 | 22.5 | 15.5 | 21.1 | 6.14 |
| 2:45 | 20.8 | 2.56 | 20 | 15.82 | 22.2 | 15.62 | 20.7 | 6.29 |
| 3:00 | 20.7 | 2.46 | 19.8 | 15.83 | 21.6 | 15.7 | 20.5 | 6.35 |
| 3:15 | 20.6 | 2.45 | 19.6 | 15.83 | 21.1 | 15.75 | 20 | 6.4 |
| 3:30 | 20.5 | 2.41 | 19.4 | 15.84 | 20.8 | 15.8 | 19.6 | 6.52 |
| 3:45 | 20.2 | 2.38 | 19.3 | 15.84 | 20.3 | 15.89 | 19.3 | 6.58 |
| 4:00 | 20.2 | 2.36 | 19.1 | 15.84 | 20.1 | 15.86 | 19.1 | 8.84 |
| 4:15 | 20.2 | 2.31 | 18.9 | 15.84 | 19.9 | 15.89 | 18.9 | 9.2 |
| 4:30 | 19.9 | 2.27 | 18.8 | 15.84 | 19.6 | 15.91 | 18.8 | 9.69 |
| 4:45 | 19.8 | 2.24 | 18.7 | 15.84 | 19.4 | 15.93 | 18.7 | 9.91 |
| 5:00 | 19.7 | 2.22 | 18.7 | 15.84 | 19.1 | 15.95 | 18.5 | 9.99 |
| Changes | 15.4 | −5.76 | 7.9 | −7.46 | 32.2 | −7.87 | 23.3 | −7.8 |

TABLE 4C

AC 300 micro + 100 micro NaOH

| Time (Min) | 1M Trial #1 Temp: C. | pH | 5M Trial #2 Temp: C. | pH | 10M Trial #3 Temp: C. | pH | 15M Trial #4 Temp: C. | pH |
|---|---|---|---|---|---|---|---|---|
| Pre-base | 18.1 | 6.35 | 16.6 | 7.6 | 16.2 | 7.5 | 15 | 7.11 |
| 0:00 | 33.8 | 12.5 | 17.2 | 15.98 | 17.1 | 15.5 | 15.8 | 15.8 |
| 0:15 | 40.6 | 11.7 | 32.5 | 4.5 | 32.5 | 12 | 47 | 10.4 |
| 0:30 | 38.5 | 11.2 | 29 | 3.76 | 29 | 10.75 | 45.3 | 10.23 |
| 0:45 | 34 | 10.45 | 27.2 | 3.61 | 27.2 | 8.5 | 40.2 | 10.13 |
| 1:00 | 36.3 | 10.66 | 26 | 3.57 | 26 | 6.94 | 34.6 | 9.23 |
| 1:15 | 27.2 | 10.81 | 24.6 | 3.5 | 24.7 | 5.44 | 31.1 | 8.73 |
| 1:30 | 25.7 | 10.83 | 23.8 | 3.44 | 24 | 3.71 | 28.3 | 7.99 |
| 1:45 | 25 | 10.9 | 23.2 | 3.46 | 22.9 | 3.55 | 27.2 | 7.17 |
| 2:00 | 24.6 | 10.89 | 22.9 | 3.46 | 22.1 | 3.45 | 25.9 | 6.15 |
| 2:15 | 23.3 | 10.84 | 22.3 | 3.49 | 21.5 | 3.23 | 23.4 | 5.2 |
| 2:30 | 22.7 | 10.77 | 22 | 3.48 | 21.1 | 3.27 | 22.5 | 4.85 |
| 2:45 | 22.1 | 10.69 | 21.7 | 3.48 | 20.7 | 3.25 | 21.8 | 4.45 |
| 3:00 | 21.8 | 10.8 | 21.3 | 3.5 | 20.4 | 3.21 | 21.3 | 4.3 |
| 3:15 | 21.4 | 10.46 | 20.9 | 3.54 | 20.1 | 3.17 | 20.8 | 4.2 |
| 3:30 | 20.8 | 10.36 | 20.5 | 3.58 | 19.8 | 3.16 | 20.5 | 4.15 |
| 3:45 | 20.7 | 10.17 | 20.3 | 3.62 | 19.5 | 3.14 | 20.1 | 4.09 |
| 4:00 | 20.5 | 10.04 | 20.3 | 3.62 | 19.3 | 3.14 | 19.8 | 4 |
| 4:15 | 20.1 | 9.91 | 20 | 3.64 | 19.1 | 3.13 | 19.5 | 4.03 |
| 4:30 | 20 | 9.68 | 19.8 | 3.66 | 19 | 3.12 | 19.2 | 4.05 |
| 4:45 | 19.8 | 9.55 | 19.6 | 3.67 | 18.8 | 3.11 | 19.1 | 4.02 |
| 5:00 | 19.6 | 9.38 | 19.4 | 3.69 | 18.6 | 3.12 | 19 | 4.02 |
| Changes | 22.5 | −6.15 | 15.9 | −8.38 | 16.3 | −8 | 32 | −8.69 |

TABLE 4D

AC 100 micro + 200 micro NaOH

| Time (Min) | 1M Trial #1 Temp: C. | pH | 5M Trial #2 Temp: C. | pH | 10M Trial #3 Temp: C. | pH |
|---|---|---|---|---|---|---|
| Pre-base | 18.6 | 6.5 | 18 | 6.23 | 17.9 | 7.3 |
| 0:00 | 20 | 14.8 | 20.3 | 15.2 | 20.6 | 15.88 |
| 0:15 | 35.2 | 11.3 | 40.7 | 13.3 | 33.9 | 14.5 |
| 0:30 | 32.6 | 10.93 | 33.2 | 13.89 | 33.4 | 14.68 |
| 0:45 | 29 | 10.48 | 29.3 | 13.94 | 31 | 14.9 |
| 1:00 | 26.5 | 10.33 | 26.6 | 13.84 | 29.9 | 15.21 |
| 1:15 | 25.3 | 10.13 | 26.2 | 13.74 | 27.2 | 15.34 |
| 1:30 | 24.3 | 10 | 25.4 | 13.61 | 26.3 | 15.55 |
| 1:45 | 23.5 | 9.87 | 24.7 | 13.51 | 24.7 | 15.73 |
| 2:00 | 23.1 | 9.8 | 24 | 13.32 | 23.7 | 15.9 |
| 2:15 | 22.8 | 9.63 | 23.4 | 13.14 | 23.3 | 15.99 |
| 2:30 | 22.3 | 9.46 | 22.9 | 12.95 | 22.9 | 16 |
| 2:45 | 22.2 | 9.29 | 22.5 | 12.56 | 22.3 | 16 |
| 3:00 | 22 | 9.08 | 22.2 | 12.23 | 21.9 | 16 |
| 3:15 | 21.8 | 8.9 | 21.6 | 11.96 | 21.6 | 16 |
| 3:30 | 21.7 | 8.6 | 21.4 | 11.74 | 21.4 | 16 |
| 3:45 | 21.5 | 8.28 | 21.2 | 11.35 | 21.2 | 16 |
| 4:00 | 21.3 | 7.88 | 21.1 | 11.01 | 20.9 | 16 |
| 4:15 | 21.3 | 7.55 | 20.9 | 10.65 | 20.6 | 16 |
| 4:30 | 21.2 | 7.14 | 20.7 | 10.5 | 20.3 | 16 |
| 4:45 | 21.1 | 6.75 | 20.5 | 10.4 | 20.2 | 16 |
| 5:00 | 21 | 6.45 | 20.4 | 10.32 | 20.1 | 16 |
| Changes | 16.6 | −8.3 | 22.7 | −8.97 | 16 | −8.58 |

TABLE 4E

AC 200 micro + 200 micro NaOH

| Time (Min) | 1M Trial #1 Temp: C. | pH | 5M Trial #2 Temp: C. | pH | 10M Trial #3 Temp: C. | pH |
|---|---|---|---|---|---|---|
| Pre-base | 17.1 | 7.7 | 16 | 7 | 15.7 | 7.8 |
| 0:00 | 18.5 | 15.68 | 17.8 | 15.9 | 19 | 15 |
| 0:15 | 31.1 | 13.9 | 36.6 | 9 | 37.6 | 11.1 |
| 0:30 | 28.3 | 13.03 | 32.3 | 9.5 | 29 | 15.2 |
| 0:45 | 27.5 | 12.91 | 26.3 | 10.7 | 26.7 | 16 |

TABLE 4E-continued

AC 200 micro + 200 micro NaOH

| Time (Min) | 1M Trial #1 Temp: C. | pH | 5M Trial #2 Temp: C. | pH | 10M Trial #3 Temp: C. | pH |
|---|---|---|---|---|---|---|
| 1:00 | 25.5 | 12.86 | 25.5 | 15.9 | 25.1 | 16 |
| 1:15 | 24.7 | 12.85 | 24.8 | 16 | 24.9 | 16 |
| 1:30 | 24.1 | 12.81 | 23 | 16 | 23.7 | 16 |
| 1:45 | 22.8 | 12.64 | 22.1 | 16 | 22.7 | 16 |
| 2:00 | 22.6 | 12.66 | 21.3 | 16 | 22.2 | 16 |
| 2:15 | 22 | 12.54 | 21 | 16 | 21.7 | 16 |
| 2:30 | 21.7 | 12.45 | 20.6 | 16 | 21.5 | 16 |
| 2:45 | 21.2 | 12.2 | 20.3 | 16 | 21 | 16 |
| 3:00 | 20.9 | 12.15 | 20.1 | 16 | 20.8 | 16 |
| 3:15 | 20.6 | 12 | 19.8 | 16 | 20.6 | 16 |
| 3:30 | 20.3 | 11.78 | 19.6 | 16 | 20.5 | 16 |
| 3:45 | 20.1 | 11.56 | 19.5 | 16 | 20.4 | 16 |
| 4:00 | 20 | 11.34 | 19.3 | 16 | 20.1 | 16 |
| 4:15 | 19.8 | 11.2 | 19.2 | 16 | 20 | 16 |
| 4:30 | 19.6 | 10.94 | 19.1 | 16 | 19.9 | 16 |
| 4:45 | 19.4 | 10.71 | 19 | 16 | 19.8 | 16 |
| 5:00 | 19.4 | 10.4 | 18.9 | 16 | 19.7 | 16 |
| Changes | 14 | −7.98 | 20.6 | −8.9 | 21.9 | −7.2 |

TABLE 4F

AC 300 micro + 200 micro NaOH

| Time (Min) | 1M Trial #1 Temp: C. | pH | 5M Trial #2 Temp: C. | pH | 10M Trial #3 Temp: C. | pH |
|---|---|---|---|---|---|---|
| Pre-base | 17.3 | 6.73 | 17.4 | 7.45 | 16 | 6.4 |
| 0:00 | 19.7 | 14.85 | 18.8 | 15.5 | 20.5 | 15.8 |
| 0:15 | 42.3 | 13.6 | 41.8 | 3.5 | 44.4 | 13.3 |
| 0:30 | 36 | 14.21 | 38.7 | 3.16 | 38.9 | 6.5 |
| 0:45 | 31.7 | 14.33 | 34.3 | 2.9 | 34.5 | 4.2 |
| 1:00 | 28.6 | 14 | 31.2 | 2.72 | 30.2 | 3.47 |
| 1:15 | 27.2 | 13.05 | 30 | 2.69 | 28.5 | 2.85 |
| 1:30 | 26.2 | 10.42 | 29.2 | 2.6 | 26.1 | 2.77 |
| 1:45 | 25.1 | 6.07 | 28.6 | 2.5 | 25 | 2.73 |
| 2:00 | 24.1 | 4.56 | 26.8 | 2.38 | 24.2 | 2.7 |

TABLE 4F-continued

AC 300 micro + 200 micro NaOH

| Time (Min) | 1M Trial #1 Temp: C. | pH | 5M Trial #2 Temp: C. | pH | 10M Trial #3 Temp: C. | pH |
|---|---|---|---|---|---|---|
| 2:15 | 23.6 | 3.35 | 26.1 | 2.34 | 23.8 | 2.67 |
| 2:30 | 23.1 | 3.26 | 25.2 | 2.29 | 23.1 | 2.65 |
| 2:45 | 22.8 | 3.232 | 25 | 2.24 | 22.6 | 2.6 |
| 3:00 | 22.3 | 3.2 | 24.8 | 2.2 | 22.2 | 2.54 |
| 3:15 | 21.9 | 3.16 | 24 | 2.18 | 21.8 | 2.52 |
| 3:30 | 21.7 | 3.15 | 23.7 | 2.14 | 21.4 | 2.48 |
| 3:45 | 21.5 | 3.11 | 23.3 | 2.09 | 21.1 | 2.42 |
| 4:00 | 21.1 | 3.09 | 22.7 | 2.05 | 20..6 | 2.4 |
| 4:15 | 21 | 3.05 | 22.3 | 2 | 20.4 | 2.39 |
| 4:30 | 20.8 | 3.03 | 22.1 | 1.97 | 20.2 | 2.38 |
| 4:45 | 20.6 | 3.02 | 21.9 | 1.94 | 20.1 | 2.37 |
| 5:00 | 20.4 | 3 | 21.5 | 1.9 | 19.9 | 2.37 |
| Changes | 25 | −8.12 | 24.4 | −8.05 | 28.4 | −9.4 |

Example 5

Acetyl Chloride Ex Vivo

Figure 6:
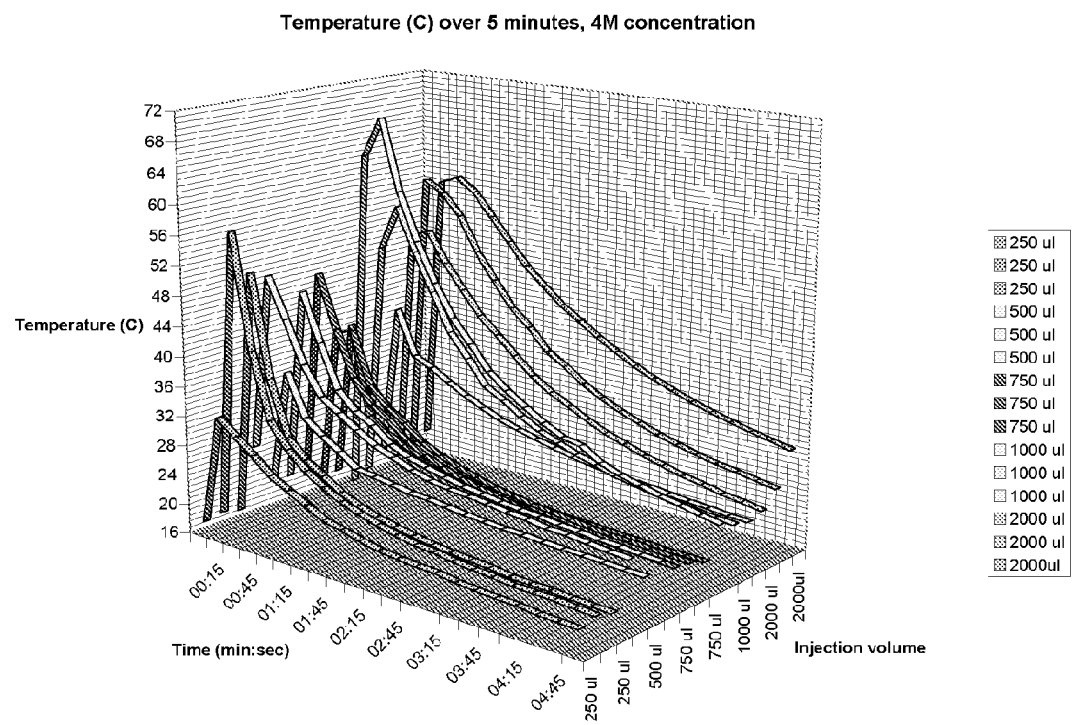
FIG. 6 is a graph of temperature changes over a 5 minute period using various amounts of a 4M acetyl chloride solution.

All injections were performed in ex vivo porcine liver brought to room temperature, using a 20 G needle with a 1 or 3 cc syringe at 1 cc over 10 seconds. The injection of acetyl chloride in diglyme was done with the needle inserted near the periphery approximately 2 cm into the tissue. An equilibrated and buffer-calibrated 18 G temperature probe was placed directly in the coagulated tissue near the injection site with measurements taken at 15 sec intervals for 5 minutes run in triplicate and averaged. Injections were performed using total volumes of 250, 500, 750, 1000, and 2000 microliters with concentrations in stepwise increments of 1, 2, and 4 molar solutions in Diglyme as exemplified in the Tables 5A-5C below. A graph of the combined average results is shown in FIG. 6.

TABLE 5A

| 1M time (min:sec) | 250 ul | 250 ul | 250 ul | average 1M 250 ul | 2000 ul | 2000 ul | 2000 ul | average 1M 2000 ul |
|---|---|---|---|---|---|---|---|---|
| 0:00 | 23.5 | 21.7 | 18.5 | 21.2 | 10.6 | 16.7 | 18.5 | 15.3 |
| 0:15 | 28.7 | 26.2 | 28.5 | 27.8 | 23.7 | 33.5 | 26.9 | 28 |
| 0:30 | 26.2 | 24.7 | 25.5 | 25.5 | 23.1 | 33.5 | 26.8 | 27.8 |
| 0:45 | 24.8 | 23.4 | 23.7 | 24 | 22 | 31.4 | 26 | 26.5 |
| 1:00 | 24.2 | 22.6 | 22.4 | 23.1 | 21.2 | 30.3 | 25.3 | 25.6 |
| 1:15 | 23.7 | 22.1 | 21.5 | 22.4 | 20.7 | 29.5 | 24.5 | 24.9 |
| 1:30 | 23.3 | 21.6 | 20.8 | 21.9 | 20.3 | 28.5 | 24.1 | 24.3 |
| 1:45 | 23 | 21.3 | 20.3 | 21.5 | 20.1 | 27.2 | 23.6 | 23.6 |
| 2:00 | 22.6 | 21 | 20 | 21.2 | 19.9 | 26.2 | 23.2 | 23.1 |
| 2:15 | 22.5 | 20.7 | 19.7 | 21 | 19.7 | 25.3 | 23 | 22.7 |
| 2:30 | 22.3 | 20.6 | 19.5 | 20.8 | 19.7 | 24.5 | 22.7 | 22.3 |
| 2:45 | 22.2 | 20.5 | 19.3 | 20.7 | 19.5 | 23.8 | 22.4 | 21.9 |
| 3:00 | 22 | 20.3 | 19.1 | 20.5 | 19.3 | 23.5 | 22.3 | 21.7 |
| 3:15 | 21.8 | 20.2 | 19 | 20.3 | 19.2 | 23 | 22 | 21.4 |
| 3:30 | 21.6 | 20.1 | 18.8 | 20.2 | 19.2 | 22.5 | 21.6 | 21.1 |
| 3:45 | 21.6 | 20.1 | 18.7 | 20.1 | 19.1 | 22.1 | 21.5 | 20.9 |
| 4:00 | 21.5 | 20 | 18.6 | 20 | 19 | 21.9 | 21.4 | 20.8 |
| 4:15 | 21.4 | 20 | 18.6 | 20 | 18.8 | 21.6 | 21.3 | 20.6 |
| 4:30 | 21.3 | 19.8 | 18.5 | 19.9 | 18.8 | 21.3 | 21.2 | 20.4 |
| 4:45 | 21.2 | 19.8 | 18.5 | 19.8 | 18.8 | 21 | 21.1 | 20.3 |
| 5:00 | 21.1 | 19.7 | 18.3 | 19.7 | 18.7 | 20.8 | 21 | 20.2 |
| Tmax (C.) | 28.7 | 26.2 | 28.5 | | 23.7 | 33.5 | 26.9 | |
| Max delta T (C.) | 5.2 | 4.5 | 10 | | 13.1 | 16.8 | 8.4 | |

TABLE 5B

| 2M time (min:sec) | 250 ul | 250 ul | 250 ul | average 2M 250 ul | 2000 ul | 2000 ul | 2000 ul | average 2M 2000 ul |
|---|---|---|---|---|---|---|---|---|
| 0:00 | 21.4 | 20.5 | 18.6 | 20.2 | 17.6 | 17.6 | 17.8 | 17.7 |
| 0:15 | 28.4 | 26.6 | 26.4 | 27.1 | 35.6 | 34.7 | 31.2 | 33.8 |
| 0:30 | 26.3 | 25.3 | 24.2 | 25.3 | 30.8 | 32.8 | 30.7 | 31.4 |
| 0:45 | 25.1 | 24.1 | 22.7 | 24 | 35.6 | 30.6 | 29.7 | 32 |
| 1:00 | 24.1 | 23.2 | 21.7 | 23 | 35.3 | 29.1 | 28.6 | 31 |
| 1:15 | 23.4 | 22.8 | 21.2 | 22.5 | 30.8 | 27.8 | 27.6 | 28.7 |
| 1:30 | 22.9 | 22.5 | 20.7 | 22 | 28.7 | 27 | 26.6 | 27.4 |
| 1:45 | 22.4 | 22.2 | 20.5 | 21.7 | 27.4 | 26.1 | 25.7 | 26.4 |
| 2:00 | 22.2 | 22.1 | 20.3 | 21.5 | 26.1 | 25.5 | 25 | 25.5 |
| 2:15 | 22 | 22 | 20.2 | 21.4 | 25.2 | 25 | 24.3 | 24.8 |
| 2:30 | 21.8 | 21.8 | 20.1 | 21.2 | 24.6 | 24.5 | 23.7 | 24.3 |
| 2:45 | 21.7 | 21.7 | 20.1 | 21.2 | 24 | 24.1 | 23.3 | 23.8 |
| 3:00 | 21.6 | 21.6 | 20 | 21.1 | 23.6 | 23.7 | 23 | 23.4 |
| 3:15 | 21.5 | 21.6 | 20 | 21 | 23.3 | 23.4 | 22.6 | 23.1 |
| 3:30 | 21.3 | 21.6 | 20 | 21 | 22.9 | 23.1 | 22.2 | 22.7 |
| 3:45 | 21.3 | 21.5 | 19.9 | 20.9 | 22.7 | 22.9 | 22 | 22.5 |

TABLE 5B-continued

| 2M time (min:sec) | 250 ul | 250 ul | 250 ul | average 2M 250 ul | 2000 ul | 2000 ul | 2000 ul | average 2M 2000 ul |
|---|---|---|---|---|---|---|---|---|
| 4:00 | 21.2 | 21.4 | 19.8 | 20.8 | 22.4 | 22.6 | 21.6 | 22.2 |
| 4:15 | 21.1 | 21.3 | 20.8 | 21.1 | 22.2 | 22.4 | 21.3 | 22 |
| 4:30 | 21 | 21.3 | 21.8 | 21.4 | 22.1 | 22.3 | 21.2 | 21.9 |
| 4:45 | 20.9 | 21.2 | 22.8 | 21.6 | 21.8 | 22.1 | 21 | 21.6 |
| 5:00 | 20.8 | 21.2 | 23.8 | 21.9 | 21.7 | 22 | 20.8 | 21.5 |
| Tmax (C.) | 28.4 | 26.6 | 26.4 | | 35.6 | 34.7 | 31.2 | |
| Max delta T (C.) | 7 | 6.1 | 7.8 | | 18 | 17.1 | 13.4 | |

TABLE 5C

| 4M time (min:sec) | 250 ul | 250 ul | 250 ul | average 4M 250 ul | 2000 ul | 2000 ul | 2000 ul | average 4M 2000 ul |
|---|---|---|---|---|---|---|---|---|
| 0:00 | 17.6 | 18 | 17.5 | 17.7 | 14.3 | 18.4 | 19.6 | 17.4 |
| 0:15 | 32.5 | 56.4 | 50.5 | 46.5 | 50.2 | 57.6 | 56.8 | 54.9 |
| 0:30 | 30.5 | 41.2 | 36.8 | 36.2 | 51.2 | 56.1 | 57.9 | 55.1 |
| 0:45 | 28.6 | 32.5 | 29.5 | 30.2 | 47.1 | 53.3 | 56.2 | 52.2 |
| 1:00 | 26.6 | 29.3 | 27.1 | 27.7 | 43.8 | 48.6 | 53.1 | 48.5 |
| 1:15 | 25.3 | 27.1 | 25.6 | 26 | 40.7 | 45.1 | 50 | 45.3 |
| 1:30 | 24.1 | 25.6 | 24.1 | 24.6 | 38.5 | 41.7 | 47 | 42.4 |
| 1:45 | 22.8 | 24.4 | 23 | 23.4 | 36.1 | 39.5 | 44.7 | 40.1 |
| 2:00 | 22.3 | 23.5 | 22.2 | 22.7 | 33.8 | 36.6 | 42.5 | 37.6 |
| 2:15 | 21.6 | 22.8 | 21.7 | 22 | 32.1 | 35.1 | 40.8 | 36 |
| 2:30 | 21.1 | 22.2 | 21.2 | 21.5 | 30.8 | 33.2 | 39.1 | 34.4 |
| 2:45 | 20.8 | 21.7 | 20.8 | 21.1 | 29.5 | 31.8 | 37.6 | 33 |
| 3:00 | 20.6 | 21.5 | 20.5 | 20.9 | 28.3 | 30.6 | 36.2 | 31.7 |
| 3:15 | 20.5 | 21.1 | 20.3 | 20.6 | 27.4 | 29.6 | 35 | 30.7 |
| 3:30 | 20.1 | 20.8 | 20.1 | 20.3 | 26.5 | 28.6 | 34 | 29.7 |
| 3:45 | 19.9 | 20.6 | 19.7 | 20.1 | 25.8 | 27.9 | 33 | 28.9 |
| 4:00 | 19.7 | 20.3 | 19.6 | 19.9 | 25.1 | 27.2 | 32.2 | 28.2 |
| 4:15 | 19.6 | 20.2 | 19.5 | 19.8 | 24.6 | 26.6 | 31.5 | 27.6 |
| 4:30 | 19.3 | 20.1 | 19.3 | 19.6 | 24 | 26.2 | 30.8 | 27 |
| 4:45 | 19.2 | 19.9 | 19.2 | 19.4 | 23.6 | 25.7 | 30.2 | 26.5 |
| 5:00 | 19.1 | 19.7 | 19.1 | 19.3 | 23.1 | 25.2 | 29.6 | 26 |
| Tmax (C.) | 32.5 | 56.4 | 50.5 | 46.4667 | 51.2 | 57.6 | 57.9 | 55.0667 |
| Max delta T (C.) | 14.9 | 38.4 | 33 | 28.7667 | 36.9 | 39.2 | 38.3 | 37.6333 |

Example 6

Ethyl Chloroformate (EC) Water Baseline

The temperature profile of the hydrolysis of ethyl chloroformate in water was first determined using the following procedure. A small volume (0.2 ml) of water was injected into a hydrophobic gel phantom consisting of a viscous, clear, colorless gel (Baby Oil Gel, Target brand or Johnson & Johnson brand). Litmus was added to the water before injecting into the gel to give it both color for better visualization in the gel and also to indicate the pH change when the ethyl chloroformate hydrolyzed. Then, the same volume of ethyl chloroformate was injected into the water bubble in the gel. This created a readily visualized spherical aqueous reaction chamber within the gel. Increasing concentrations of ethyl chloroformate solutions in diglyme were used from (from 0.5M to 5M).

Figure 7:
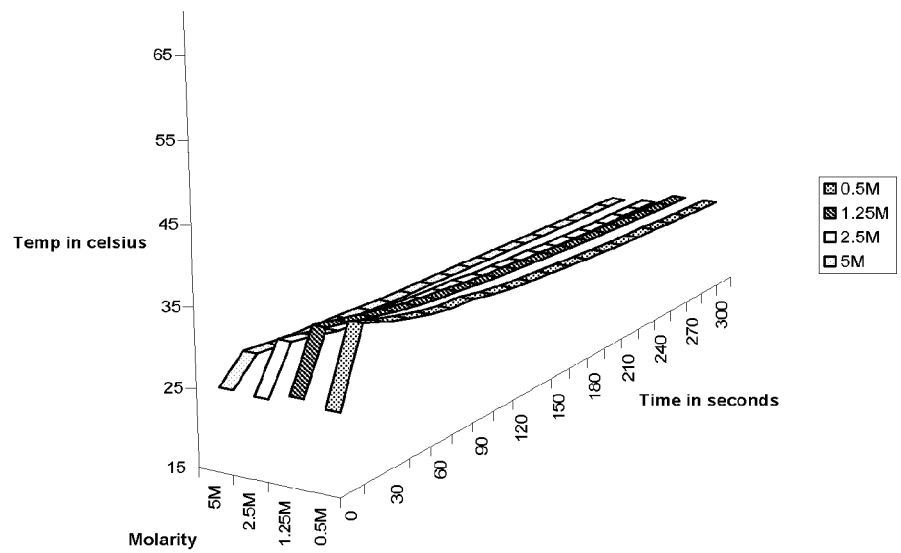
FIG. 7 is a graph of temperature change of various amounts of ethyl chloroformate in water.

A thermocouple probe was positioned 0.5 cm away from the center of the aqueous reaction mixture and the reaction temperature (° C.) was measured every 15 seconds for 5 minutes. A baseline temperature was recorded in the water bubble before adding the ethyl chloroformate. Each reaction was performed in triplicate with the results shown below in Tables 6A-6D. The average temperatures over all concentrations were graphed as a function of both reagent concentration (molarity) and time (seconds), and are shown in FIG. 7.

TABLE 6A

| | 200 microliters of 0.5M Ethyl Chloroformate + 200 microliters of water | | | |
|---|---|---|---|---|
| Time (sec) | ° C. | ° C. | ° C. | Average ° C. |
| 0 | 23.2 | 23.4 | 23.6 | 23.40 |
| 15 | 32 | 32 | 31.8 | 31.93 |
| 30 | 30.9 | 30.2 | 30.7 | 30.60 |
| 45 | 29.6 | 29.5 | 29.8 | 29.63 |
| 60 | 28.2 | 29 | 29.2 | 28.80 |
| 75 | 28.1 | 28.6 | 28.4 | 28.37 |
| 90 | 27.6 | 28.1 | 27.9 | 27.87 |
| 105 | 26.8 | 27.6 | 27.6 | 27.33 |
| 120 | 27.1 | 27.1 | 27.3 | 27.17 |
| 135 | 26.9 | 26.7 | 27 | 26.87 |
| 150 | 26.6 | 26.6 | 26.7 | 26.63 |
| 165 | 26.3 | 26.4 | 26.4 | 26.37 |
| 180 | 26.1 | 26.2 | 26.1 | 26.13 |
| 195 | 25.8 | 26 | 26 | 25.93 |
| 210 | 25.4 | 25.9 | 25.9 | 25.73 |
| 225 | 25.4 | 25.7 | 25.5 | 25.53 |
| 240 | 25.4 | 25.5 | 25.6 | 25.50 |
| 255 | 25.2 | 25.5 | 25.5 | 25.40 |
| 270 | 25.1 | 25.4 | 25.3 | 25.27 |

TABLE 6A-continued 200 microliters of 0.5M Ethyl Chloroformate +
200 microliters of water

| Time (sec) | ° C. | ° C. | ° C. | Average ° C. |
|---|---|---|---|---|
| 285 | 25 | 25.2 | 25.2 | 25.13 |
| 300 | 24.9 | 25 | 25.1 | 25.00 |

TABLE 6B 200 microliters of 1.25M Ethyl Chloroformate +
200 microliters of water

| Time (sec) | ° C. | ° C. | ° C. | Average ° C. |
|---|---|---|---|---|
| 0 | 25.2 | 25.2 | 25.2 | 25.20 |
| 15 | 32 | 33 | 32.7 | 32.57 |
| 30 | 31.2 | 32.3 | 32.2 | 31.90 |
| 45 | 30.5 | 31.6 | 31.6 | 31.23 |
| 60 | 29.7 | 30.9 | 30.9 | 30.50 |
| 75 | 29.4 | 30.2 | 30.3 | 29.97 |
| 90 | 29.1 | 29.8 | 29.8 | 29.57 |
| 105 | 28.8 | 29.6 | 29.4 | 29.27 |
| 120 | 28.5 | 29.2 | 29 | 28.90 |
| 135 | 28.3 | 28.9 | 28.7 | 28.63 |
| 150 | 28.2 | 28.6 | 28.6 | 28.47 |
| 165 | 27.9 | 28.4 | 28.3 | 28.20 |
| 180 | 27.7 | 28.2 | 28.1 | 28.00 |
| 195 | 27.5 | 28 | 27.8 | 27.77 |
| 210 | 27.2 | 27.8 | 27.7 | 27.57 |
| 225 | 27.2 | 27.7 | 27.6 | 27.50 |
| 240 | 27 | 27.5 | 27.4 | 27.30 |
| 255 | 26.9 | 27.4 | 27.2 | 27.17 |
| 270 | 26.8 | 27.2 | 27.2 | 27.07 |
| 285 | 26.7 | 27.1 | 27 | 26.93 |
| 300 | 26.7 | 27 | 27 | 26.90 |

TABLE 6C 200 microliters of 2.5M Ethyl Chloroformate +
200 microliters of water

| Time (sec) | ° C. | ° C. | ° C. | Average ° C. |
|---|---|---|---|---|
| 0 | 24 | 24.4 | 24.5 | 24.30 |
| 15 | 30 | 29.9 | 30.2 | 30.03 |
| 30 | 29 | 29.6 | 29.6 | 29.40 |
| 45 | 28.4 | 29 | 28.6 | 28.67 |
| 60 | 27.9 | 28.9 | 28.5 | 28.43 |
| 75 | 27.4 | 28.7 | 28.3 | 28.13 |
| 90 | 27 | 28.2 | 28 | 27.73 |
| 105 | 26.9 | 27.8 | 27.8 | 27.50 |
| 120 | 26.5 | 27.7 | 27.5 | 27.23 |
| 135 | 26.5 | 27.7 | 27.2 | 27.13 |
| 150 | 26.2 | 27.3 | 26.8 | 26.77 |
| 165 | 26 | 27.2 | 26.7 | 26.63 |
| 180 | 25.7 | 27.1 | 26.6 | 26.47 |
| 195 | 25.6 | 26.9 | 26.5 | 26.33 |
| 210 | 25.4 | 26.6 | 26.2 | 26.07 |
| 225 | 25.3 | 26.5 | 26.2 | 26.00 |
| 240 | 25.3 | 26.3 | 25.9 | 25.83 |
| 255 | 25.2 | 26.2 | 25.8 | 25.73 |
| 270 | 25.2 | 26.2 | 26 | 25.80 |
| 285 | 25.1 | 26.1 | 25.9 | 25.70 |
| 300 | 25.1 | 25.8 | 25.9 | 25.60 |

TABLE 6D 200 microliters of 5M Ethyl Chloroformate +
200 microliters of water

| Time (sec) | ° C. | ° C. | ° C. | Average ° C. |
|---|---|---|---|---|
| 0 | 24.6 | 24.6 | 24.6 | 24.60 |
| 15 | 27.4 | 28 | 27.9 | 27.77 |
| 30 | 26.9 | 27.8 | 27.4 | 27.37 |
| 45 | 26.5 | 27.4 | 27.2 | 27.03 |
| 60 | 26.3 | 27.3 | 27.1 | 26.90 |
| 75 | 26.2 | 27.1 | 27 | 26.77 |
| 90 | 26.2 | 26.8 | 26.7 | 26.57 |
| 105 | 26 | 26.7 | 26.3 | 26.33 |
| 120 | 25.8 | 26.5 | 26.4 | 26.23 |
| 135 | 25.8 | 26.5 | 26.3 | 26.20 |
| 150 | 25.8 | 26.3 | 26.2 | 26.10 |
| 165 | 25.8 | 26.2 | 26.1 | 26.03 |
| 180 | 25.7 | 26.1 | 26 | 25.93 |
| 195 | 25.6 | 26 | 25.9 | 25.83 |
| 210 | 25.5 | 25.8 | 25.9 | 25.73 |
| 225 | 25.5 | 25.7 | 25.8 | 25.67 |
| 240 | 25.4 | 25.6 | 25.7 | 25.57 |
| 255 | 25.3 | 25.5 | 25.6 | 25.47 |
| 270 | 25.3 | 25.5 | 25.7 | 25.50 |
| 285 | 25.3 | 25.4 | 25.6 | 25.43 |
| 300 | 25.3 | 25.3 | 25.3 | 25.30 |

Example 7

Ethyl Chloroformate (EC) in NaOH

The temperature profile of the hydrolysis of ethyl chloroformate using one equivalent of base (e.g. 200 μl of 5M ethyl chloroformate+400 μl of 2.5M NaOH) and two equivalents of base (e.g. 200 μl of 5M ethyl chloroformate+400 μl of 5M NaOH) were then determined. The process was similar to that of Example 6, with the NaOH solution injected into the gel phantom after mixing with the litmus (rather than the baseline water injection). Increasing concentrations of ethyl chloroformate solutions in diglyme from 2.5M to 10M were then injected. The rest of the process followed that of Example 6, with the results shown below in Tables 7A-7D.

TABLE 7A 200 microliters of 5M EC + 400 microliters of 5M NaOH

| Time (sec) | ° C. | ° C. | ° C. | Average ° C. |
|---|---|---|---|---|
| 0 | 20.2 | 20.5 | 20.6 | 20.43 |
| 5 | 47.6 | 48.6 | 47.9 | 48.03 |
| 10 | 48.2 | 49.6 | 48.7 | 48.83 |
| 15 | 49.4 | 49.8 | 49.6 | 49.60 |
| 30 | 49.3 | 48.5 | 48.6 | 48.80 |
| 45 | 48.5 | 47.6 | 47.8 | 47.97 |
| 60 | 47 | 46.1 | 46.6 | 46.57 |
| 75 | 45.4 | 44.8 | 45.4 | 45.20 |
| 90 | 42.8 | 42.8 | 43.9 | 43.17 |
| 105 | 41.9 | 41.7 | 42.7 | 42.10 |
| 120 | 40.9 | 40.8 | 41.5 | 41.07 |
| 135 | 39.4 | 39.9 | 40.2 | 39.83 |
| 150 | 38.6 | 39.1 | 38.7 | 38.80 |
| 165 | 37.7 | 38.5 | 37.8 | 38.00 |
| 180 | 36.9 | 37.5 | 37.1 | 37.17 |
| 195 | 36.1 | 36.6 | 36.4 | 36.37 |
| 210 | 35.4 | 35.8 | 35.7 | 35.63 |
| 225 | 34.7 | 35.1 | 35.2 | 35.00 |
| 240 | 34 | 34.4 | 34.6 | 34.33 |
| 255 | 33.4 | 33.2 | 34.1 | 33.57 |
| 270 | 32.7 | 32.8 | 33.5 | 33.00 |
| 285 | 32.2 | 32.5 | 32.8 | 32.50 |
| 300 | 31.7 | 32.2 | 32.3 | 32.07 |

TABLE 7B 200 microliters of 2.5M Ethyl Chloroformate (EC) + 400 microliters of 1.25M NaOH

| Time (sec) | ° C. | ° C. | ° C. | Average ° C. |
|---|---|---|---|---|
| 0 | 24 | 24.3 | 24.7 | 24.33 |
| 5 | 32.3 | 33 | 31.6 | 32.30 |
| 10 | 34.2 | 33.9 | 33.8 | 33.97 |
| 15 | 35.1 | 34.8 | 35.2 | 35.03 |
| 30 | 35 | 34.6 | 35.1 | 34.90 |
| 45 | 34.8 | 34.2 | 34.8 | 34.60 |
| 60 | 34.7 | 33.8 | 34.6 | 34.37 |
| 75 | 34.5 | 33.7 | 34.3 | 34.17 |
| 90 | 34.2 | 33.4 | 34.1 | 33.90 |
| 105 | 33.9 | 33.1 | 34 | 33.67 |
| 120 | 33.5 | 32.9 | 33.8 | 33.40 |
| 135 | 33.3 | 32.5 | 33.5 | 33.10 |
| 150 | 33.1 | 32.2 | 33.1 | 32.80 |
| 165 | 32.8 | 31.9 | 32.7 | 32.47 |
| 180 | 32.7 | 31.6 | 32.3 | 32.20 |
| 195 | 32.5 | 31.3 | 32.1 | 31.97 |
| 210 | 32.2 | 31.2 | 31.8 | 31.73 |
| 225 | 31.7 | 31.1 | 31.4 | 31.40 |
| 240 | 31.4 | 31 | 31.1 | 31.17 |
| 255 | 31.1 | 30.8 | 30.9 | 30.93 |
| 270 | 30.5 | 30.6 | 30.4 | 30.50 |
| 285 | 29.9 | 30.2 | 30.2 | 30.10 |
| 300 | 29.5 | 29.9 | 29.8 | 29.73 |

TABLE 7C 200 microliters of 5M EC + 400 microliters of 2.5M NaOH

| Time (sec) | ° C. | ° C. | ° C. | Average ° C. |
|---|---|---|---|---|
| 0 | 24 | 24.8 | 25.1 | 24.63 |
| 5 | 38.8 | 38.9 | 40.1 | 39.27 |
| 10 | 39.1 | 39.1 | 40.4 | 39.53 |
| 15 | 39.9 | 39.2 | 40.6 | 39.90 |
| 30 | 39.7 | 38.7 | 40.3 | 39.57 |
| 45 | 39.2 | 37.9 | 39.7 | 38.93 |
| 60 | 38.9 | 37.3 | 39.1 | 38.43 |
| 75 | 38.3 | 36.1 | 38.4 | 37.60 |
| 90 | 37.9 | 35.8 | 37.7 | 37.13 |
| 105 | 37.4 | 35.5 | 37.1 | 36.67 |
| 120 | 36.9 | 35 | 36.6 | 36.17 |
| 135 | 36.4 | 34.7 | 36.3 | 35.80 |
| 150 | 35.8 | 34.4 | 35.8 | 35.33 |
| 165 | 35.4 | 34 | 35.4 | 34.93 |
| 180 | 34.7 | 33.7 | 34.7 | 34.37 |
| 195 | 34.1 | 33.3 | 33.6 | 33.67 |
| 210 | 33.6 | 32.9 | 33.1 | 33.20 |
| 225 | 32.8 | 32.6 | 32.9 | 32.77 |
| 240 | 32.1 | 32.3 | 32.6 | 32.33 |
| 255 | 31.4 | 32.2 | 32.1 | 31.90 |
| 270 | 30.8 | 31.9 | 32 | 31.57 |
| 285 | 30.4 | 31.7 | 31.8 | 31.30 |
| 300 | 30.1 | 31.5 | 31.7 | 31.10 |

TABLE 7D 200 microliters of 10M EC + 400 microliters of 5M NaOH

| Time (sec) | ° C. | ° C. | ° C. | Average ° C. |
|---|---|---|---|---|
| 0 | 24.5 | 25 | 25.2 | 24.90 |
| 5 | 58.3 | 59.1 | 57.2 | 58.20 |
| 10 | 59.1 | 59.7 | 58.5 | 59.10 |
| 15 | 60.2 | 60.9 | 59.2 | 60.10 |
| 30 | 59.1 | 60.1 | 58.6 | 59.27 |
| 45 | 58.3 | 59.4 | 57.4 | 58.37 |
| 60 | 57.2 | 58.3 | 56.6 | 57.37 |
| 75 | 55.6 | 56.7 | 55.4 | 55.90 |
| 90 | 53.8 | 55.2 | 53.2 | 54.07 |
| 105 | 51.9 | 53.8 | 51.3 | 52.33 |
| 120 | 50.3 | 52.1 | 50.8 | 51.07 |
| 135 | 48.3 | 50.6 | 48.2 | 49.03 |
| 150 | 46.2 | 48.6 | 47.1 | 47.30 |
| 165 | 45.1 | 46.2 | 45.3 | 45.53 |
| 180 | 44.2 | 45.3 | 44.1 | 44.53 |
| 195 | 43.4 | 43.8 | 42.7 | 43.30 |
| 210 | 42.5 | 42.6 | 41.2 | 42.10 |
| 225 | 41.8 | 41.9 | 40.5 | 41.40 |
| 240 | 41.1 | 41.2 | 39.1 | 40.47 |
| 255 | 40.4 | 40.6 | 38.4 | 39.80 |
| 270 | 39.2 | 39.7 | 37.7 | 38.87 |
| 285 | 38.1 | 39.1 | 37.3 | 38.17 |
| 300 | 37.2 | 38.7 | 36.4 | 37.43 |

Example 8

Ethyl Chloroformate (EC) with NaOH Ex Vivo

The temperature profile of the hydrolysis of ethyl chloroformate by one equivalent of base in ex vivo pig livers was then determined. Increasing concentrations of ethyl chloroformate solutions in diglyme from 2.5M to 10M were used. It was noted that the ethyl chloroformate reacted in the coaxial device and formed a precipitate. Therefore, the ethyl chloroformate and the NaOH were mixed in a vial and quickly injected into the ex vivo pig livers. A thermocouple probe was placed 1 cm from the injected needle tip and baseline temperature was recorded before injecting the reaction mixture. The temperature measurement (° C.) was recorded every 15 seconds for 5 minutes from the hydrolysis of ethyl chloroformate by aqueous NaOH in ex. vivo liver. Each reaction was performed in triplicate. The results are shown below in Tables 8A-8D.

The hydrolysis of ethyl chloroformate is known to be slower in acidic and neutral pH. That could account for the observed lower Tmax with increasing concentrations of ethyl chloroformate solutions in diglyme when they were hydrolyzed in water. As expected, the hydrolysis of ethyl chloroformate in an alkaline environment was much faster and the Tmax increased with increasing concentrations of ethyl chloroformate solutions. Although the Tmax of the hydrolysis of ethyl chloroformate by NaOH in the gel phantom was higher than in the ex vivo pig liver, the baseline temperature in the ex vivo pig liver was lower. Furthermore, the change in temperature between the Tmax and the baseline for the highest concentration of ethyl chloroformate (10M) in the ex vivo pig liver was 28.4° C.

Figure 8:
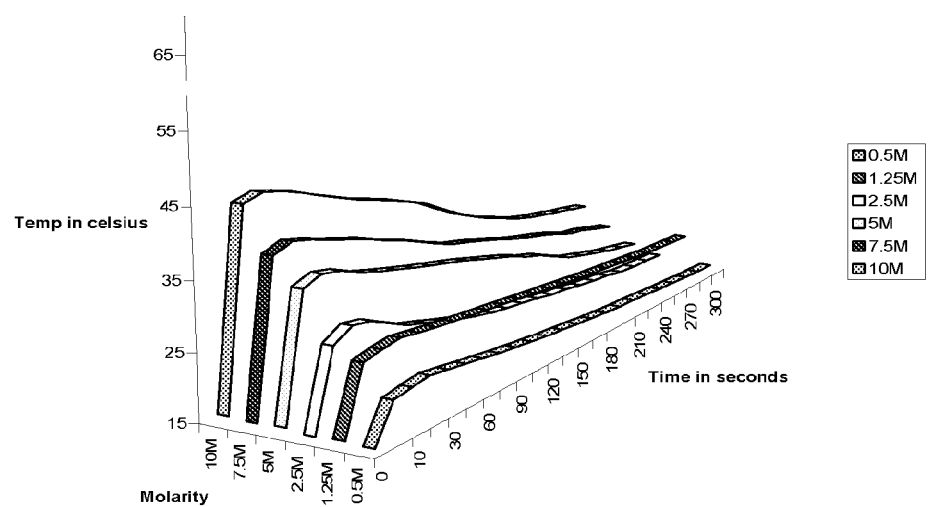
FIG. 8 is a graph of temperature changes following injection of a solution of ethyl chloroformate and sodium hydroxide in ex vivo liver samples.

A graph of the average temperatures over all concentrations as a function of both reagent concentration (molarity) and time (seconds) is shown in FIG. 8. The NaOH was half the concentration of the ethyl chloroformate in each reaction but twice the volume. The largest temperature change from the baseline was 28.4° C. in the 10M ethyl chloroformate reaction.

TABLE 8A 200 microliters of 2.5M EC + 400 microliters of 1.25M NaOH

| Time (sec) | ° C. | ° C. | ° C. | Average ° C. |
|---|---|---|---|---|
| 0 | 15.4 | 15.2 | 15.7 | 15.43 |
| 5 | 26.2 | 27.3 | 26.8 | 26.77 |

TABLE 8A-continued 200 microliters of 2.5M EC + 400 microliters of 1.25M NaOH

| Time (sec) | ° C. | ° C. | ° C. | Average ° C. |
|---|---|---|---|---|
| 10 | 28.1 | 28.6 | 28.4 | 28.37 |
| 15 | 27.3 | 28.2 | 27.9 | 27.80 |
| 30 | 25.5 | 27.1 | 26.2 | 26.27 |
| 45 | 24.1 | 25.4 | 24.9 | 24.80 |
| 60 | 23.4 | 24.1 | 24.3 | 23.93 |
| 75 | 22.5 | 23.3 | 23.1 | 22.97 |
| 90 | 21.5 | 22.1 | 22.7 | 22.10 |
| 105 | 20.8 | 21.4 | 21.8 | 21.33 |
| 120 | 20.2 | 20.8 | 21.2 | 20.73 |
| 135 | 19.8 | 20.4 | 20.6 | 20.27 |
| 150 | 19.6 | 19.9 | 20.1 | 19.87 |
| 165 | 19.3 | 19.5 | 19.7 | 19.50 |
| 180 | 18.9 | 18.7 | 19.2 | 18.93 |
| 195 | 18.8 | 18.3 | 18.8 | 18.63 |
| 210 | 18.6 | 17.4 | 18.4 | 18.13 |
| 225 | 18.3 | 17.1 | 17.9 | 17.77 |
| 240 | 18.1 | 16.9 | 17.5 | 17.50 |
| 255 | 17.2 | 16.8 | 17 | 17.00 |
| 270 | 17 | 16.6 | 16.8 | 16.80 |
| 285 | 16.9 | 16.5 | 16.7 | 16.70 |
| 300 | 16.8 | 16.3 | 16.5 | 16.53 |

TABLE 8B 200 microliters of 5M EC + 400 microliters of 2.5M NaOH

| Time (sec) | ° C. | ° C. | ° C. | Average ° C. |
|---|---|---|---|---|
| 0 | 15.8 | 15.9 | 16 | 15.90 |
| 5 | 33.6 | 34.4 | 33.8 | 33.93 |
| 10 | 34.7 | 34.9 | 35.1 | 34.90 |
| 15 | 33.8 | 34.1 | 34.7 | 34.20 |
| 30 | 32.1 | 33.2 | 33.2 | 32.83 |
| 45 | 31.6 | 32.3 | 31.8 | 31.90 |
| 60 | 30.9 | 31.4 | 30.9 | 31.07 |
| 75 | 30.1 | 30.5 | 30.1 | 30.23 |
| 90 | 29.4 | 29.8 | 29.2 | 29.47 |
| 105 | 28.8 | 29.1 | 28.3 | 28.73 |
| 120 | 28 | 28.3 | 27.6 | 27.97 |
| 135 | 27.3 | 27.6 | 26.4 | 27.10 |
| 150 | 26.2 | 27 | 25.5 | 26.23 |
| 165 | 25.1 | 26.2 | 24.8 | 25.37 |
| 180 | 24 | 24.6 | 24.1 | 24.23 |
| 195 | 22.8 | 23.8 | 23.6 | 23.40 |
| 210 | 21.3 | 22.4 | 22.7 | 22.13 |
| 225 | 19.9 | 21.3 | 21.5 | 20.90 |
| 240 | 19.3 | 20.4 | 20.8 | 20.17 |
| 255 | 18.6 | 19.8 | 19.9 | 19.43 |
| 270 | 18.1 | 19.3 | 19.1 | 18.83 |
| 285 | 17.8 | 18.7 | 18.5 | 18.33 |
| 300 | 17.6 | 18.1 | 17.8 | 17.83 |

TABLE 8C 200 microliters of 7.5M EC + 400 microliters of NaOH

| Time (sec) | ° C. | ° C. | ° C. | Average ° C. |
|---|---|---|---|---|
| 0 | 15.3 | 16.2 | 15.6 | 15.70 |
| 5 | 37.6 | 36.8 | 39.1 | 37.83 |
| 10 | 38.9 | 37.6 | 39.8 | 38.77 |
| 15 | 38.4 | 37 | 38.4 | 37.93 |
| 30 | 37.2 | 36.1 | 37.1 | 36.80 |
| 45 | 36.5 | 34.8 | 36.3 | 35.87 |
| 60 | 35.8 | 33.2 | 35.5 | 34.83 |
| 75 | 35.1 | 31.4 | 34.2 | 33.57 |
| 90 | 34.2 | 30.3 | 33.1 | 32.53 |
| 105 | 32.8 | 29.5 | 31.5 | 31.27 |
| 120 | 31.4 | 28.7 | 29.8 | 29.97 |
| 135 | 30.3 | 27.9 | 28.3 | 28.83 |
| 150 | 29.5 | 27.2 | 27.6 | 28.10 |

TABLE 8C-continued 200 microliters of 7.5M EC + 400 microliters of NaOH

| Time (sec) | ° C. | ° C. | ° C. | Average ° C. |
|---|---|---|---|---|
| 165 | 28.3 | 26.4 | 27.1 | 27.27 |
| 180 | 27.1 | 25.7 | 26.4 | 26.40 |
| 195 | 26.3 | 24.8 | 25.1 | 25.40 |
| 210 | 25.6 | 24.1 | 24.3 | 24.67 |
| 225 | 24.8 | 23.6 | 23.4 | 23.93 |
| 240 | 24.1 | 22.7 | 22.5 | 23.10 |
| 255 | 23.5 | 21.5 | 21.3 | 22.10 |
| 270 | 22.8 | 21.1 | 21.3 | 21.73 |
| 285 | 21.5 | 20.7 | 20.6 | 20.93 |
| 300 | 20.7 | 20.2 | 19.8 | 20.23 |

TABLE 8D 200 microliters of 10M EC + 400 microliters of NaOH

| Time (sec) | ° C. | ° C. | ° C. | Average ° C. |
|---|---|---|---|---|
| 0 | 16.2 | 15.8 | 15.9 | 15.97 |
| 5 | 43.8 | 44.3 | 44.8 | 44.30 |
| 10 | 44.2 | 45.1 | 45.4 | 44.90 |
| 15 | 43.5 | 44.6 | 44.2 | 44.10 |
| 30 | 42.1 | 43.5 | 43.1 | 42.90 |
| 45 | 41.2 | 41.7 | 41.7 | 41.53 |
| 60 | 40.3 | 40.1 | 40.4 | 40.27 |
| 75 | 39.4 | 38.4 | 39.2 | 39.00 |
| 90 | 38.5 | 37.3 | 38.1 | 37.97 |
| 105 | 37.6 | 36.5 | 36.8 | 36.97 |
| 120 | 36.2 | 35.2 | 35.7 | 35.70 |
| 135 | 34.7 | 34.3 | 34.4 | 34.47 |
| 150 | 32.1 | 32.7 | 33.2 | 32.67 |
| 165 | 30.2 | 31.1 | 31.5 | 30.93 |
| 180 | 28.4 | 29.8 | 30.1 | 29.43 |
| 195 | 27.5 | 28.3 | 28.6 | 28.13 |
| 210 | 26.3 | 27.4 | 27.7 | 27.13 |
| 225 | 25.6 | 26.3 | 26.3 | 26.07 |
| 240 | 25.1 | 25.4 | 25.4 | 25.30 |
| 255 | 24.7 | 24.6 | 24.8 | 24.70 |
| 270 | 24.3 | 24 | 24.2 | 24.17 |
| 285 | 23.8 | 23.5 | 23.7 | 23.67 |
| 300 | 23.4 | 22.8 | 23.1 | 23.10 |

A number of embodiments of the invention have been described. Nevertheless, it will be understood that various modifications may be made without departing from the spirit and scope of the invention. Accordingly, other embodiments are within the scope of the following claims.

What is claimed is:

1. A thermochemical ablation system, comprising:
a percutaneous fluid delivery cannula comprising a first lumen extending from a proximal portion to a distal portion, the distal portion comprising a first port in fluid communication with at least the first lumen;
a first reservoir containing a highly reactive electrophilic reagent in fluid communication with the first lumen of the percutaneous fluid delivery cannula, at least a portion of the highly reactive electrophilic reagent being deliverable out of the first port to locally generate ablation heat at a targeted site and to provide a localized residual acidic environment at the targeted site for a period of time after generation of the ablation heat; and
a real-time imaging system that monitors the distal portion of the percutaneous fluid delivery cannula and the delivery of the highly reactive electrophilic reagent.

2. The system of claim 1, wherein the percutaneous fluid delivery cannula comprises a generally rigid injection needle.

3. The system of claim 2, wherein the injection needle comprises an outside diameter of about 0.134 inches or less.

4. The system of claim 1, wherein the highly reactive electrophilic reagent is deliverable from the first port so as to react with nucleophiles inherently present at the targeted site to locally generate ablation heat sufficient to ablate bodily tissue proximate the distal portion of the percutaneous fluid delivery cannula.

5. The system of claim 4, wherein the nucleophiles inherently present at the targeted site comprise naturally occurring proteins disposed in the bodily tissue.

6. The system of claim 1, further comprising:
a second lumen extending from a proximal portion of the percutaneous delivery cannula to a distal portion of the cannula, the distal portion comprising a second port in fluid communication with at least the second lumen; and
a second reservoir to communicate a nucleophile reagent through the second lumen to the distal portion of the percutaneous fluid delivery cannula, at least a portion of the nucleophile reagent being deliverable out of the second port prior to delivery of the highly reactive electrophilic reagent out of the first port.

7. The system of claim 6, wherein the nucleophile reagent is delivered from the second port first in order to pre-treat the targeted site, and the highly reactive electrophilic reagent is subsequently delivered from the first port so that the reagents mix with one another at the targeted site to locally generate an exothermic chemical reaction.

8. The system of claim 7, wherein the exothermic chemical reaction generates heat sufficient to ablate bodily tissue proximate the distal portion of the percutaneous fluid delivery cannula.

9. The system of claim 1, wherein the highly reactive electrophilic reagent comprises a carboxylic acid anhydride or halide.

10. The system of claim 9, wherein the nucleophile reagent comprises a base.

11. The system of claim 1, wherein the percutaneous fluid delivery cannula comprises a flexible catheter.

12. A method for thermochemical ablation of targeted tissue, comprising:
delivering a highly reactive electrophilic reagent through a lumen of a percutaneous injection needle to a targeted tissue site; and
reacting the delivered electrophilic reagent with nucleophiles at the targeted tissue location to locally generate ablation heat at the targeted tissue site and to provide a localized residual acidic environment at the targeted tissue site for a period of time after generation of the ablation heat.

13. The method of claim 12, wherein the highly reactive electrophilic reagent is delivered from one or more side ports of the injection needle.

14. The method of claim 12, wherein the highly reactive electrophilic reagent comprises a carboxylic acid anhydride.

15. The method of claim 12, wherein the highly reactive electrophilic reagent comprises acetic anhydride.

16. The method of claim 12, wherein the highly reactive electrophilic reagent comprises a carboxylic halide.

17. The method of claim 12, wherein the highly reactive electrophilic reagent comprises an acetyl halide.

18. The method of claim 12, wherein the highly reactive electrophilic reagent comprises acetyl chloride.

19. The method of claim 12, wherein the highly reactive electrophilic reagent comprises a sulfonyl acid anhydride or halide.

20. The method of claim 12, wherein the highly reactive electrophilic reagent comprises a phosphonyl acid anhydride or halide.

21. The method of claim 12, wherein the highly reactive electrophilic reagent further comprises a diagnostic group usable for imaging or tracing purposes.

22. The method of claim 12, wherein the highly reactive electrophilic reagent comprises one or more electrophilic leaving group species.

23. The method of claim 12, wherein the highly reactive electrophilic reagent comprises one or more diagnostic leaving groups usable for imaging or tracing purposes.

24. The method of claim 12, further comprising delivering a nucleophile reagent to the targeted tissue site prior to delivering the highly reactive electrophilic reagent to the targeted tissue site.

25. The method of claim 24, wherein the nucleophile reagent comprises a base.

26. The method of claim 25, wherein the nucleophile reagent comprises a base selected from the group consisting of KOH, NaOH, $NH_4OH$, $Ca(OH)_2$, $NaHCO_3$, $K_2CO_2$, BuLi, NaOEt or NaSEt, amines, and combinations thereof.

27. The method of claim 12, further comprising delivering an inert, non-reactive agent to the targeted tissue site.

28. The method of claim 27, wherein the inert, non-reactive agent comprises a diagnostic agent.

29. The method of claim 12, further comprising monitoring the targeted tissue site with real-time imaging.

30. The method of claim 29, wherein real-time imaging comprises CT, ultrasound, MRI, or other imaging system.

31. A method for thermochemical ablation of targeted tissue, comprising delivering a highly reactive electrophilic reagent to a targeted tissue to generate heat in a localized area in order to ablate the targeted tissue area.

32. The method of claim 31, wherein the highly reactive electrophilic reagent comprises an inorganic or organic chloride.

33. The method of claim 31, wherein the highly reactive electrophilic reagent comprises an inorganic acid halide.

34. The method of claim 31, wherein the highly reactive electrophilic reagent comprises acetyl chloride.

35. The method of claim 31, wherein the highly reactive electrophilic reagent comprises ethyl chloroformate.

36. The method of claim 31, further comprising pre-treating the targeted tissue area with a nucleophilic reagent.

37. The method of claim 36, wherein the nucleophilic reagent comprises an inorganic or organic base.

38. The method of claim 36, wherein the nucleophilic reagent comprises sodium hydroxide or potassium hydroxide.

* * * * *